US008318492B2

(12) United States Patent
Choo et al.

(10) Patent No.: US 8,318,492 B2
(45) Date of Patent: Nov. 27, 2012

(54) METHOD FOR DETERMINING THE CELL CULTURE HISTORY OF A CELL UNIT LABELED WITH MORE THAN ONE TYPE OF TAG

(75) Inventors: Yen Choo, London (GB); Fraser Hornby, Andover (GB); John Girdlestone, Borehamwood (GB)

(73) Assignee: Plasticell Limited, London (GB)

( * ) Notice: Subject to any disclaimer, the term of this patent is extended or adjusted under 35 U.S.C. 154(b) by 723 days.

(21) Appl. No.: 12/072,457

(22) Filed: Feb. 25, 2008

(65) Prior Publication Data

US 2009/0029368 A1 Jan. 29, 2009

Related U.S. Application Data

(63) Continuation of application No. PCT/GB2006/003186, filed on Aug. 25, 2006.

(30) Foreign Application Priority Data

Aug. 26, 2005 (GB) .................................. 0517382.8
Aug. 25, 2006 (WO) ....................... PCT/GB06/03186

(51) Int. Cl.
 *C12N 5/02* (2006.01)
 *C12N 5/00* (2006.01)
 *G01N 37/00* (2006.01)

(52) U.S. Cl. ........ 435/403; 435/325; 435/373; 435/378; 435/380; 435/383; 435/395; 435/396; 435/397; 435/402; 436/518; 436/523; 436/524; 436/528; 436/534; 436/56; 436/172; 436/176; 436/177

(58) Field of Classification Search .................. 436/518, 436/523, 527, 528–533, 56, 176, 524, 10, 436/172, 177; 435/373, 378, 380, 395–397, 435/402–403, 325, 383
See application file for complete search history.

(56) References Cited

U.S. PATENT DOCUMENTS

| | | | | |
|---|---|---|---|---|
| 5,789,261 | A * | 8/1998 | Schwartz | ...................... 436/518 |
| 5,990,479 | A | 11/1999 | Weiss | |
| 6,207,392 | B1 | 3/2001 | Weiss | |
| 6,251,303 | B1 | 6/2001 | Bawendi | |
| 6,319,426 | B1 | 11/2001 | Bawendi | |
| 6,322,901 | B1 | 11/2001 | Bawendi | |
| 6,423,551 | B1 | 7/2002 | Weiss | |
| 6,426,513 | B1 | 7/2002 | Bawendi | |
| 6,444,143 | B2 | 9/2002 | Bawendi | |
| 6,576,291 | B2 | 6/2003 | Bawendi | |
| 6,649,138 | B2 | 11/2003 | Adams | |
| 6,815,064 | B2 | 11/2004 | Treadway | |
| 2002/0045045 | A1 | 4/2002 | Adams | |
| 2003/0017264 | A1 | 1/2003 | Treadway | |
| 2007/0298411 | A1 * | 12/2007 | Choo | .............................. 435/6 |

FOREIGN PATENT DOCUMENTS

WO WO-98/19161 5/1998
WO WO-2004/031639 A1 4/2004

OTHER PUBLICATIONS

Duke Scientific Corporation, Reagent Microsphere-Surface Properties and Conjugation Methods, Technical Note—013C, May 1, 2004).*
Sheila R. Nicewarner-Pena, et al.; "Submicrometer Metallic Barcodes"; Science, American Association for the Advancement of Science; vol. 294; No. 5540; Oct. 5, 2001; pp. 137-141.
B. M. Desay, et al.; "Mechanisms of Muscle Stem Cell Expansion with Cytokines"; Stem Cells, Alphamed Press; Dayton, Oh; Jan. 2002; pp. 50-60.
Joel S. Greenberger, et al.; "Expansion of Hemaqtopoietic Stem Cells In Vitro as a Model System for Human Tissue Engineering"; The Orthopedic Clinics of North America; Jul. 2000; vol. 31; No. 3; pp. 499-510.
International Search Report dated Oct. 18, 2006.
Duke Scientitic Corporation, Regent Microsphere-Surface Properties and Conjugation Methods, Technical Note—013C, May 1, 2004.
Wener et al. "Cultivation of Immortalized Human Hepatocytes HepZ on Macroporous CultiSpher G Microcarriers," *Biotechnology and Bioengineering* (2000) vol. 68, No. 1, pp. 59-70.
Rasey et el. "Growth and radiation of cells grown in macrophorous gelatin microcarriers (CultiSpher-G™)," *British Journal of Cancer* (1996) vol. 74, pp. S78-S81.
Raihan et el. "Immobilization of whole bacterial cells for anaerobic biotransformations," *Applied Microbiology and Biotechnology* (1997) vol. 47, No. 4, pp. 352-357.
Xiao et al. "High density and scale-up cultivation of recombinant CHO cell line and hybridomas with porous microcarrier Cytopore," *Cytotechnology* (1999) vol. 30, pp. 143-147.
Bücheler et al. "Tissue Engineering of Human Salivary Gland Organoids," *Acta Otolaryngol* (2002) vol. 122, No. 5, pp. 541-545.
Guiles et al. "A Visual Tagging Process for Mix and Sort Combinatorial Chemistry," *Angew. Chemical Int. Ed.* (1998) vol. 37, No. 7, pp. 926-928.
*Stem Cells: Scientific Process and Future Research Directions.* Department of Health and Human Services. Jun. 2001. </info/scireport/2001report>.
Gordon, Siamon and Philip Taylor. "Monocyte and Macrophage Heterogeneity," *Immunology* (2005) vol. 5, pp. 953-964.
Kaushansky, Kenneth. "Lineage-Specific Hematopoietic Growth Factors," *New England Journal of Medicine* (2006) vol. 354, No. 19, pp. 2034-2045.
Godin, Isabelle and Ana Cumano. "The Hare and the Tortoise: An Embryonic Haemetopoietic Race," *Immunology* (2002) vol. 2, pp. 593-603.
Zhaolie et al. "Study of a re-PA production by recombinant CHO calls immobilized with a porous microcarrier," *Chinese Journal of Biotechnology* (1999) vol. 15, No. 4, pp. 450-454.
Zhaolie et al. "Study of a re-PA production by recombinant CHO calls immobilized with a porous microcarrier," English Abstract, *Chinese Journal of Biotechnology* (1999) vol. 15, No. 4, pp. 450-454.

* cited by examiner

*Primary Examiner* — Gail R Gabel
(74) *Attorney, Agent, or Firm* — Steptoe & Johnson LLP

(57) ABSTRACT

The present invention relates in one aspect to a method for determining the cell culture history of a cell unit labelled with more than one type of tag comprising the steps of: (a) measuring one or more parameters of each tag that is used to label the cell unit; (b) identifying each tag in the cell unit; and (c) correlating the identity of each tag to the identity of the cell unit and/or the specific cell culture conditions to which the cell unit has been exposed.

27 Claims, 20 Drawing Sheets t = 0 t = 45m t = 1hr 30m

METHOD FOR DETERMINING THE CELL CULTURE HISTORY OF A CELL UNIT LABELED WITH MORE THAN ONE TYPE OF TAG

RELATED APPLICATIONS

This is a continuation patent application that claims priority to PCT patent application number PCT/GB2006/003186, filed on Aug. 25, 2006, which claims priority to GB application number 0517382.8, filed on Aug. 26, 2005, the entirety of which are herein incorporated by reference.

FIELD OF THE INVENTION

The invention broadly relates to cell culture—such as the culture of primary cells, cell lines, pluripotent cells, totipotent cells and stem cells.

BACKGROUND TO THE INVENTION

Over recent years cell culture has become a core technology in the life sciences. Cell culture is described in 'Basic Cell Culture' Oxford University Press (2002) Ed. J. M. Davis; and 'Animal Cell Culture' Oxford University Press (2000) Ed. John R. W. Masters; both of which are incorporated herein in their entirety by reference. Cell culture provides the basis for studying cellular processes such as the viability, phenotype, genotype, proliferation and differentiation of cells, and the formation of biological molecules, intermediates and products. It has also provided the means to study the regulation of these processes, from the genetic level—whether in isolation or in whole transgenic animals—down to the level of individual protein molecules. Notwithstanding its enormous contribution to the current state of biology, in many respects cell culture remains a developing discipline, albeit an unusually exciting science ultimately offering the possibility of genetic therapy and tissue engineering.

An important goal of cell culture is to be able to grow a wide variety of cells in vitro. The list of different cell types that can be grown in culture is extensive (see American Type Culture collection; European Collection of Cell Cultures, Deutsche Sammlung von Mikroorganismen and Zellkulturen GmbH,), includes representatives of most cell types, and is continually increasing as more and more culture conditions are discovered. Despite the steady progress in the field, the method of determining suitable culture conditions for new cell types remains totally empirical: growth conditions are almost always discovered by trial and error. The choice of starting point will often be based on what was previously used by others for similar cells, or even what is currently being used in the laboratory for different cells. Many times these will simply be completely inadequate, and a process of trial and error must begin anew. Even when new culture conditions are successful, it is worthwhile remembering that adaptations of previous protocols will have introduced a historical bias to the experiment. For instance, much of the early tissue culture experiments made extensive use of fibroblasts, and to this date most standard cell culture conditions favour growth of cells derived from the mesoderm (fibroblasts, endothelium, myoblasts). The development of selective growth media for epithelial and other cell types based on these conditions was a challenge. For some of these cell types it is now known that serum—a normal component of many culture media for mesodermal cells—actually inhibits growth. One aspect of the invention described herein is a method for developing suitable culture conditions which allow for the viability, proliferation or growth, and retention of the phenotype of particular cell types.

Some common problems which are still encountered in cell culture are the limited lifespan of primary cell lines, the change of characteristics of cell lines with passage, and their transformation accompanied by loss of interesting cellular characteristics. These effects severely limit the utility of cultured cells for use in experiments or assays, for instance cell-based assays described below. Primary cells, i.e. cells freshly isolated from tissues, offer by far the most accurate cell culture models, as they behave in a way that broadly resembles their tissue of origin. Remarkably, a reliable method of culturing primary cells has still not been developed and consequently these cells exhibit a limited lifespan in vitro. This presents a serious technical limitation, for instance when attempting to amplify the primary culture, or when attempting to perform a longer-term experiment. A further problem associated with the use of primary cultures is that since they require constant fresh isolation, it can be hard to source primary material, particularly from humans and it is also difficult to obtain lines that behave consistently. A third aspect of the invention is therefore a method of culturing primary cells to obtain viable cultures with a prolonged lifespan.

If primary cultures are maintained in vitro for an extended period, they normally undergo a crisis in which the majority of cells perish, however the surviving cells are longer lived and can be cultured indefinitely. Most of these continuous cell lines are almost invariably poor representations of the cell as it is found in intact animal tissues. One reason for this lies in the fact that the process that allows the cells to become immortal also has an impact on the characteristics of the cell. For example, most established cell cultures have stopped expressing tissue-specific genes and instead only express housekeeping genes required for continuous growth in cell culture—as a result most such cell lines are more like each other than like the tissue from which they were originally sourced. For instance, most liver cell lines have stopped expressing the drug-metabolizing enzymes that would normally make them interesting tools for testing drug toxicity. A further aspect of the invention described herein is a method of culturing cells so that they provide more accurate models of tissues. This in turn would improve the reliability and predictive power of cell-based experiments and assays.

Improved techniques for culturing cells and methods for discovering and implementing such techniques for regulation of cellular processes such as growth, differentiation, metabolic activity, and phenotypic expression are presented in our co-pending international application WO 2004/031369. When handling large numbers of cell units, their identity and/or cell culture history (for example, the chronology and the exact nature of a series of culture conditions that any one group or unit may have been exposed to) can become confused. WO2004/031369 describes improved methods for determining the identity and/or cell culture history of cell units. In one aspect there is described the use of cell units which can be handled conveniently in cell biology experiments, enabling for example the splitting and pooling of said units.

The present invention seeks to provide further improvements which overcome some of the limitations of the prior art.

SUMMARY OF THE INVENTION

In a first aspect, there is provided a method for determining the cell culture history of a cell unit labelled with more than one tag (e.g. type of tag) comprising the steps of: (a) measuring one or more parameters of each tag that is used to label the cell unit; (b) identifying each tag in the cell unit; and (c) correlating the identity of each tag to the identity of the cell unit and/or the specific cell culture conditions to which the cell unit has been exposed.

In a further aspect, there is provided a computer program product including a computer program for controlling a computer to perform the method described herein.

In a further aspect, there is provided an apparatus for determining the cell culture history of a cell unit comprising data processing logic operable to perform data processing operations in accordance with the method described herein.

In a further aspect, there is provided a complex comprising a microcarrier and a charged (e.g. negatively charged) tag.

In a further aspect, there is provided a complex comprising a microcarrier and a rod-shaped tag.

The qualities of the tags that are described herein can advantageously be utilised in conjunction with the improvements that are disclosed herein. Such improvements comprise for example the improved labelling of specific types of tag and specific types of cell unit, the improved separation of tags from cell units and the improved analysis of tags.

In a further aspect, there is provided a method for separating a complex comprising a microcarrier and a tag, comprising the step of contacting said complex with a protease, wherein said microcarrier comprises, consists or consists essentially of protein.

In a further aspect, there is provided a method for separating a complex comprising a microcarrier and a tag, comprising the step of contacting said complex with acid.

Advantageously, these methods can be used to separate a cell unit and a tag in such a way that the tag can be analysed using the methods described herein. Moreover, these methods do not result in tags that are spoiled by such treatment. Still further, these methods address the problem of the tags being obtained in a manner which seriously complicates their analysis—such as the tags becoming dispersed over a large surface area and/or floating on a denser aqueous solution.

In a further aspect, there is provided a method for determining the effect of a plurality of culture conditions on a cell comprising the use of the complex described herein.

In a further aspect, there is provided a method for determining the effect of a plurality of culture conditions on a cell, comprising the steps of: (a) providing a first set of groups of cell units each comprising one or more cells, and exposing said groups to desired culture conditions; (b) pooling two or more of said groups to form at least one second pool; (c) subdividing the second pool to create a further set of groups of cell units; (d) exposing said further groups to desired culture conditions; (e) optionally, repeating steps (b)-(d) iteratively as required; and (f) assessing the effect on a given cell unit of the culture conditions to which it has been exposed, wherein each cell unit comprises one or more cells adherent to or bounded by the complex described herein.

In a further aspect, there is provided a method for exposing a cell to a variety of cell culture conditions, comprising the steps of: (a) providing a first set of groups of cell units each comprising one or more cells, and exposing said groups to desired culture conditions; (b) pooling two or more of said groups to form at least one second pool; (c) subdividing the second pool to create a further set of groups of cell units; (d) exposing said further groups to desired culture conditions; and (e) optionally, repeating steps (b)-(d) iteratively as required, wherein each cell unit comprises one or more cells adherent to or bounded by the complex described herein.

In a further aspect, there is provided a method for determining the effect of a plurality of culture conditions on a cell, comprising the steps of: (a) providing a first set of groups of cell units each comprising one or more cells, and exposing said groups to desired culture conditions; (b) pooling two or more of said groups to form at least one second pool; (c) subdividing the second pool to create a further set of groups of cell units; (d) exposing said further groups to desired culture conditions; (e) optionally, repeating steps (b)-(d) iteratively as required; and (f) assessing the effect on a given cell unit of the culture conditions to which it has been exposed, wherein each cell unit comprises one or more cells adherent to or bounded by the complex described herein.

In a further aspect, there is provided a method for identifying a gene which influences a cellular process, comprising the steps of: a) determining the effect of one or more culture conditions on a cell unit, in accordance with the methods described herein; b) analysing gene expression in said cell units when exposed to said culture conditions; and c) identifying genes which are differentially expressed under desired culture conditions.

In a further aspect, there is provided a method for producing a nucleic acid which encodes a gene product which influences a cellular process, comprising identifying a gene in accordance with the method described herein, and producing at least the coding region of said gene by nucleic acid synthesis or biological replication.

In a further aspect, there is provided a method for inducing a cellular process, comprising the steps of: (a) identifying one or more genes which are differentially expressed in association with the cellular process in accordance with the method described herein; and (b) modulating the expression of said one or more genes in the cell.

In a further aspect, there is provided a method for identifying the state of a cellular process of a cell, comprising the steps of: (a) identifying one or more genes which are differentially expressed in association with the cellular process in accordance with the method described herein; and (b) detecting the modulation of expression of said one or more genes in a cell, thereby determining the state of the cellular process of said cell.

In a further aspect, there is provided a method for inducing a cellular process, comprising the steps of: (a) determining the effect of one or more culture conditions on a cell unit, in accordance with the methods described herein; (b) exposing a cell to culture conditions which induce the cellular process; and (c) isolating the desired cell.

In a further aspect, there is provided a method for identifying an agent which is capable of inducing a cellular process, comprising the steps of: (a) determining the effect of one or more agents on a cell unit, in accordance with the methods described herein; and (bj identifying those agent(s) which induce the cellular process in the cell units.

In a further aspect, there is provided a method for preparing an agent which is capable of inducing a cellular process, comprising the steps of: (a) determining the effect of one or more agents on a cell unit, in accordance with the methods described herein; (b) identifying those agent(s) which induce the desired cellular process in the cell units; and c) synthesising or isolating the agent(s).

In a further aspect, there is provided a method for culturing stem cells or cells that have been derived from stem cells in vitro comprising the steps of: a) incubating a stem cell culture; and b) splitting said culture into two or more groups of stem cells, and culturing said group of stem cells under two or more different sets of culture conditions, wherein the cells are cultured in cell units, each cell unit comprising one or more cells adhered to or bounded by the complex described herein.

In a further aspect, there is provided a method for culturing stem cells, comprising growing said stem cells adhered to the complex described herein.

In a further aspect, there is provided a method for obtaining differentiated cells from stem cells in vitro, comprising the steps of: (a) growing stem cells adherent to the complex described herein in a culture medium; (b) transferring the complex from one culture medium to another; (c) optionally repeating step (b) as required; and (d) obtaining the differentiated cells attached to the complex.

In a further aspect, there is provided a method of growing pluripotent stem cells in vitro comprising the steps of: (a) seeding said cells on the complex described herein; and (b) propagating the cells while attached to the complex.

In a further aspect, there is provided a method for culturing cells in vitro or in vitro, comprising growing said cells adhered to the complex described herein In a further aspect, there is provided a method for identifying a tag obtained or obtainable from a cell unit comprising the steps of: (a) separating the cell unit and the tag; (b) obtaining one or more images of the tag using a microscopic technique; and (c) analysing the images to determine one or more features of the tag.

In a further aspect, there is provided the use of the complex described herein for determining the effect of a plurality of culture conditions on a cell.

In a further aspect, there is provided the use of a rod-shaped tag—such as a nanowire to label a microcarrier.

In a further aspect, there is provided the use of a rod-shaped tag—such as a nanowire for determining the effect of a plurality of culture conditions on a cell.

In a further aspect, there is provided a method, a complex, a computer program, an apparatus or a use substantially as described herein with reference to the accompanying figures.

EMBODIMENTS

In some embodiments, the method is an automated method.

In some embodiments, the cell unit is bound or adhered to a microcarrier.

In some embodiments, the microcarrier is a porous or a solid microcarrier.

In some embodiments, the porous microcarrier is selected from the group consisting of CYTOPORE microcarrier (e.g. a CYTOPORE 1 microcarrier or a CYTOPORE 2 microcarrier), a CULTISPHER microcarrier, a CULTISPHER-G microcarrier, a CULTISPHER-GL microcarrier and a CULTISPHER-S microcarrier, an INFORMATRIX microcarrier, a MICROSPHERE microcarrier, a SIRAN microcarrier, and a MICROPOROUS MC microcarrier.

In some embodiments, the solid microcarrier is selected from the group consisting of a CYTODEX microcarrier (e.g. a CYTODEX 1, CYTODEX 2 or CYTODEX 3 microcarrier) a BIOSILON microcarrier, a BIOGLASS microcarrier, a FACT III microcarrier or a DE 52/53 microcarrier.

In some embodiments, the parameter(s) are the size of the tags and/or the optical properties of the tags, In some embodiments, the optical properties are selected from the group consisting of: light reflectivity, colour, the fluorescence emission wavelength(s) and the fluorescence emission intensity.

In some embodiments, one or more image(s) of each tag in the cell unit in the field of interest is measured.

In some embodiments, one or more image(s) of each tag in the cell unit in the field of interest is measured using microscopy.

In some embodiments, the microscopy method is selected fro the group consisting of bright field microscopy, phase-contrast microscopy, oblique illumination microscopy, dark field microscopy, differential interference contrast microscopy, reflection contrast microscopy, varel contrast microscopy, polarizing microscopy, interference microscopy and fluorescence microscopy.

In some embodiments, outlines are drawn for the one or more image(s) of each tag in the cell unit in the field of interest.

In some embodiments, one or more fluorescence image(s) of each tag in the cell unit in the field of interest is measured.

In some embodiments, outlines for the one or more image(s) are loaded onto the one or more fluorescence image(s).

In some embodiments, one or more fluorescence image(s) of each tag in the cell unit in the field of interest is measured for each fluorophore that is used to label the tags.

In some embodiments, each tag in the cell unit is identified by reading the one or more parameters of the tag within the one or more outlines.

In some embodiments, the one or more parameters of the tag are the area and/or optical density of the tag.

In some embodiments, the one or more parameters of the tag are inputted into a spreadsheet.

In some embodiments, the fluorophore is selected from the group consisting of a fluorophore that emits a blue, green, near red or far red fluorescence.

In some embodiments, where two or more fluorophores are used, the fluorophores do not quench each other.

In some embodiments, the sizes are selected from at least 3 different sizes—such as 4, 5, 6 or 7 different sizes.

In some embodiments, the sizes are selected from the group consisting of about 1.9 µm, about 4.4 µm, about 5.4 µm, about 5.8 µm, about 7.4 µm, about 9.7 µm and about 9.8 µm In some embodiments, the fluorophore is selected from the group consisting of UV2, Starfire Red and TRITC.

In some embodiments, the quantity of fluorophore is selected from 5 different quantities.

In some embodiments, these quantities are indicated by ranges (e.g. ranges of fluorescence intensity).

In some embodiments, each different quantity gives about a 5 to 10-fold difference in brightness.

In some embodiments, there are at least 2 different parameters.

In some embodiments, there are at least 5 different integers.

In some embodiments, the microcarrier is a porous microcarrier.

In some embodiments, the microcarrier has a net charge.

In some embodiments, the microcarrier comprises, consists or consists essentially of protein, cellulose, polyethylene, polystyrol, glass, collagen, collagen-gylcose-aminoglycan and/or gelatin.

In some embodiments, the tag has a charge.
In some embodiments, the tag has a net charge.
In some embodiments, the tag has a negative charge.
In some embodiments, the charged tag is a sphere.
In some embodiments, the sphere is a microsphere.
In some embodiments, the microsphere is about 9 µM or less in diameter.

In some embodiments, the microsphere is a carboxylate modified (CML) microsphere.

In some embodiments, the tag comprises, consists or consists essentially of polystyrene.

In some embodiments, the complex (e.g. the microcarrier) is adhered or bound to a cell unit.

In some embodiments, at least one antibody is bound to the cell unit.

In some embodiments, the rod-shaped tag is a nanowire.

In some embodiments, the nanowire is an aluminium nanowire.

In some embodiments, the nanowire is coated with silver and/or gold.

In some embodiments, the nanowire is about 1 μM or less in diameter.

In some embodiments, the nanowire is about 10 μM or less in length.

In some embodiments, the microcarrier is a porous microcarrier.

In some embodiments, the porous microcarrier is a charge neutral microcarrier.

In some embodiments, at least one antibody is bound to the cell unit.

In some embodiments, the microcarrier comprises, consists or consists essentially of gelatin.

In some embodiments, the microcarrier is a CULTISPHER microcarrier.

In some embodiments, the microcarrier is selected from the group consisting of a CULTISPHER-G microcarrier, a CULTISPHER-GL microcarrier and CULTISPHER-S microcarrier.

In some embodiments, the protease is selected from the group consisting of proteinase K, typsin, thermolysin and caspase.

In some embodiments, the proteinase K is used in an amount of about 0.5 U/ml or less.

In some embodiments, the complex is contacted with proteinase K for at least 20-60 minutes.

In some embodiments, the complex is contacted with the protease in a volume of about 5 μl or less.

In some embodiments, the microcarrier comprises, consists or consists essentially of cellulose.

In some embodiments, the microcarrier is a CYTOPORE microcarrier.

In some embodiments, the microcarrier is a CYTOPORE 2 microcarrier.

In some embodiments, the tag is a sphere.

In some embodiments, the acid is selected from the group consisting of hydrochloric acid, sulphuric acid and sodium hypochlorite.

In some embodiments, the acid is 37% hydrochloric acid (~12M).

In some embodiments, the acid is concentrated sulphuric acid.

In some embodiments, the complex is contacted with acid in a volume of about 5 μl or less.

In some embodiments, the complex is heated in the presence of the acid.

In some embodiments, the cells are cultured in cell units, each cell unit comprising one or more cells.

In some embodiments, the cell units are single cells.

In some embodiments, the culture conditions are media to which the cell is exposed.

In some embodiments, the media contain one or more specific agents which influence a cellular process.

In some embodiments, the cell culture conditions comprise culturing at one or more specific temperatures.

In some embodiments, the cell culture conditions comprise culturing on one or more specific substrates.

In some embodiments, the desired culture conditions influence a cellular process.

In some embodiments, modulation of gene expression in the cell comprises transfection of said one or more genes into the cell.

In some embodiments, modulation of gene expression comprises the exogenous administration of a gene product.

In some embodiments, said one or more genes encode a marker.

In some embodiments, said marker may be detected by an immunoassay.

In some embodiments, the cellular process is cell proliferation or differentiation.

In some embodiments, the cell units are single cells.

In some embodiments, said stem cells are subjected to at least one change of culture conditions.

In some embodiments, said change of culture conditions comprises a change of medium.

In some embodiments, the differentiated cells are isolated by enzymatic or chemical detachment from the complex.

In some embodiments, the differentiated cells are isolated by digestion of the complex.

DESCRIPTION OF THE FIGURES

FIG. 2 shows CULTISPHER-G microcarriers trapped on a 70 μm filter during washes to remove unbound, microbeads (size range 4.4 μm-9.8 μm), which pass through.

In further detail, box (a) shows that the lower limit for a first parameter is less than the mean measurement for a first parameter and the upper limit for a first parameter is greater than the mean measurement for a first parameter; box (b) shows that the lower limit for a second parameter is less than the mean measurement for a second parameter and the upper limit for a second parameter is greater than the mean measurement for a second parameter; boxes (c), (f) (i), (k), (o), (q), (t) and (v) each show that the mean measurement for a third parameter is greater than the lower limit for the third parameter; box (e) shows that if the result from box (b) is negative then the upper, lower and mean measurements for a further integer of a parameter are measured. In particular, box (e) shows that the lower area limit for an integer of a parameter is less than the mean measurement of the parameter and that the upper area limit for the integer of the parameter is greater than the mean measurement of the parameter. This is repeated for further integers of a parameter in boxes (h), (j), (n), (p), (s) and (u).

Figure 6:
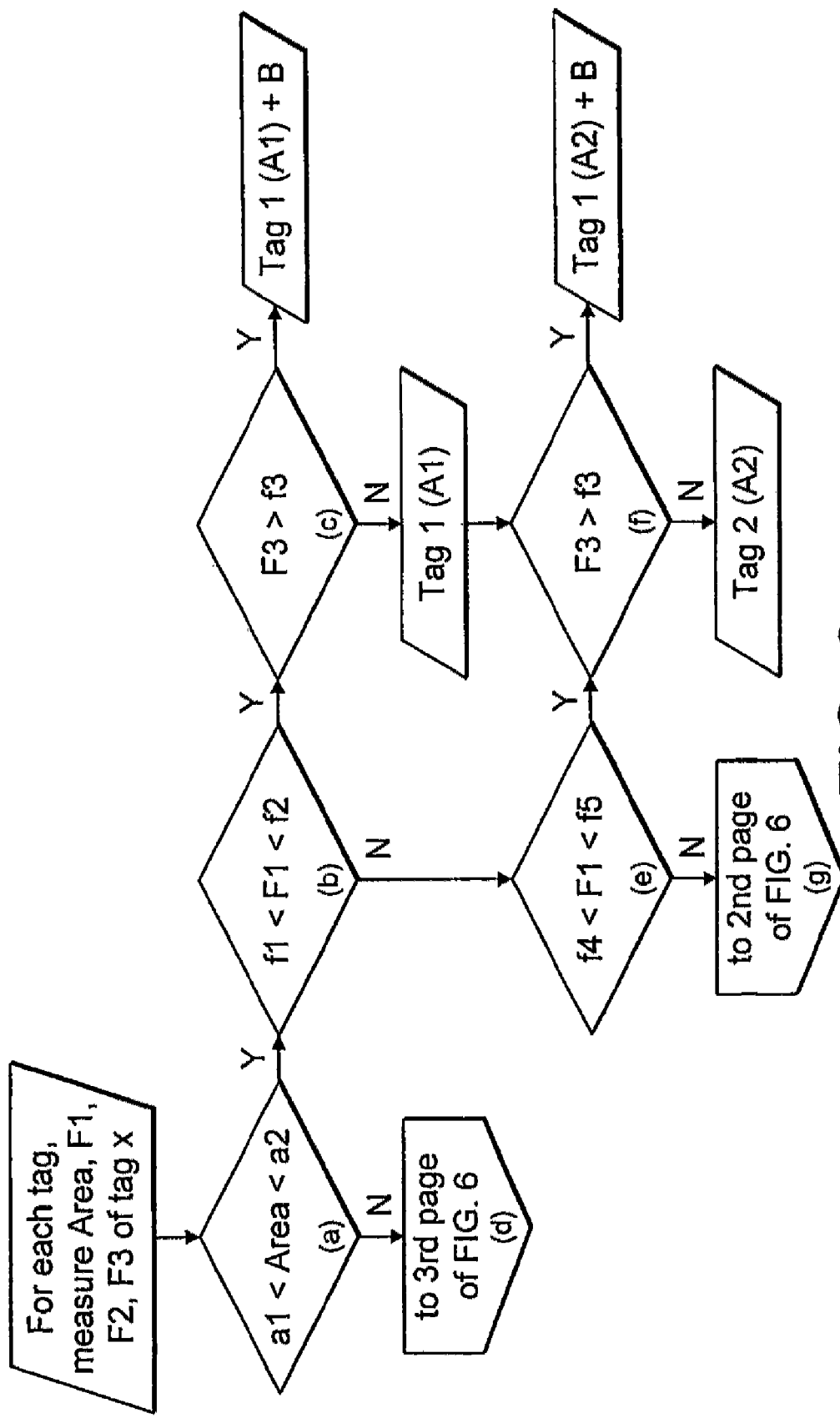
FIG. 6 shows a Tag ID Flowchart in which the microbeads (tags) are of 2 different sizes, each with 4 levels of fluorophore A±fluorophore B. Fluorophore A is UV2 and Fluororophore B is TRITC. F1—mean optical density measurement for tag using UV2 channel; F2—mean optical density measurement for tag using Starfire Red channel; F3—mean optical density measurement for tag using TRITC channel; f1—lower limit for fluorescence of tag 1; f2—upper limit for fluorescence of tag 1; f3—lower threshold for TRITC fluorescence of all tags; f4—lower limit for fluorescence of tag 2; f5—upper limit for fluorescence of tag 2 etc; Area—area measurement; a1—lower area limit for tag of size 1; a2—upper area limit for tag of size 1; a3—lower area limit for tag of size 2; a4—upper area limit for tag of size 2 etc; Y=yes; N=no.
Figure 6:
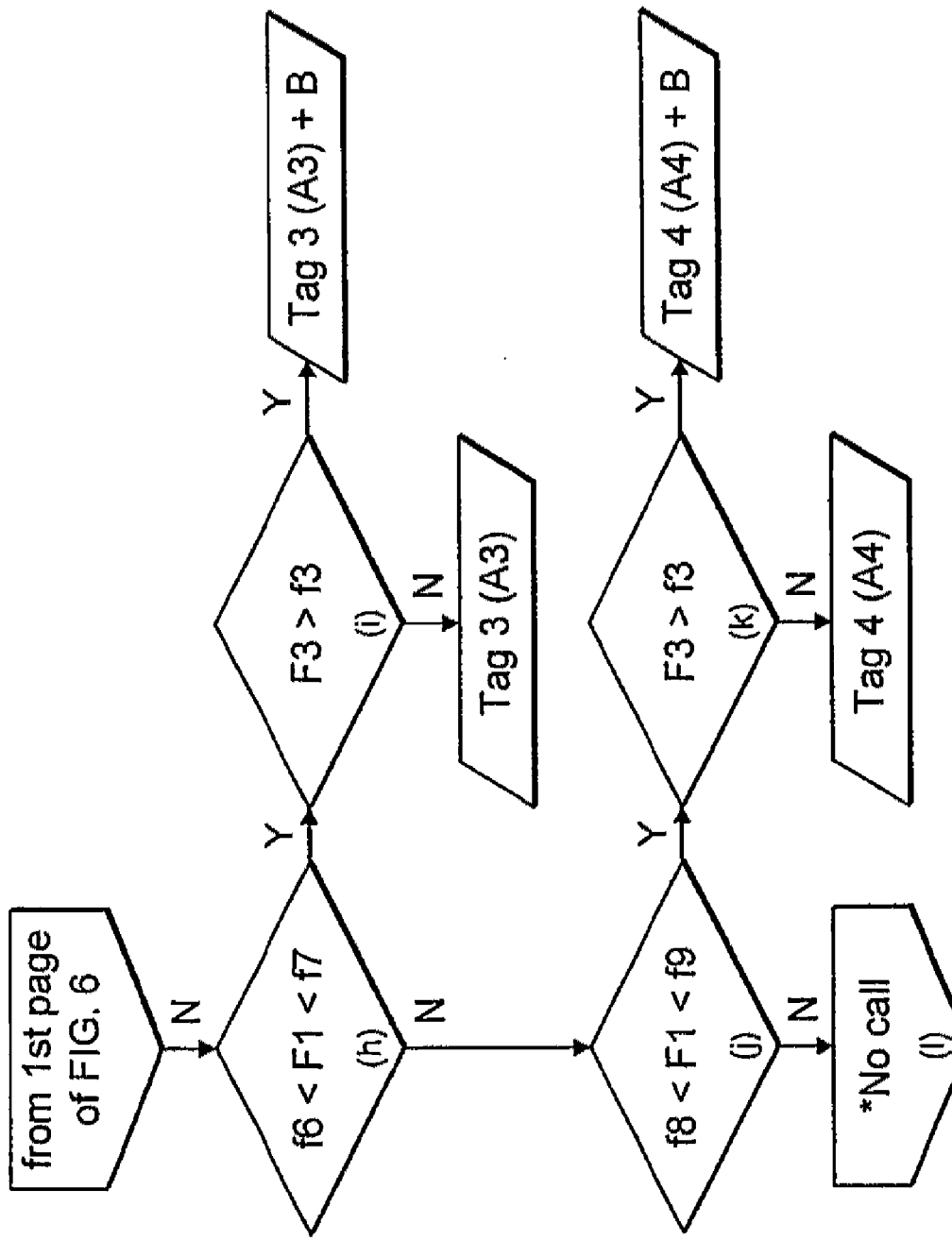
Figure 6:
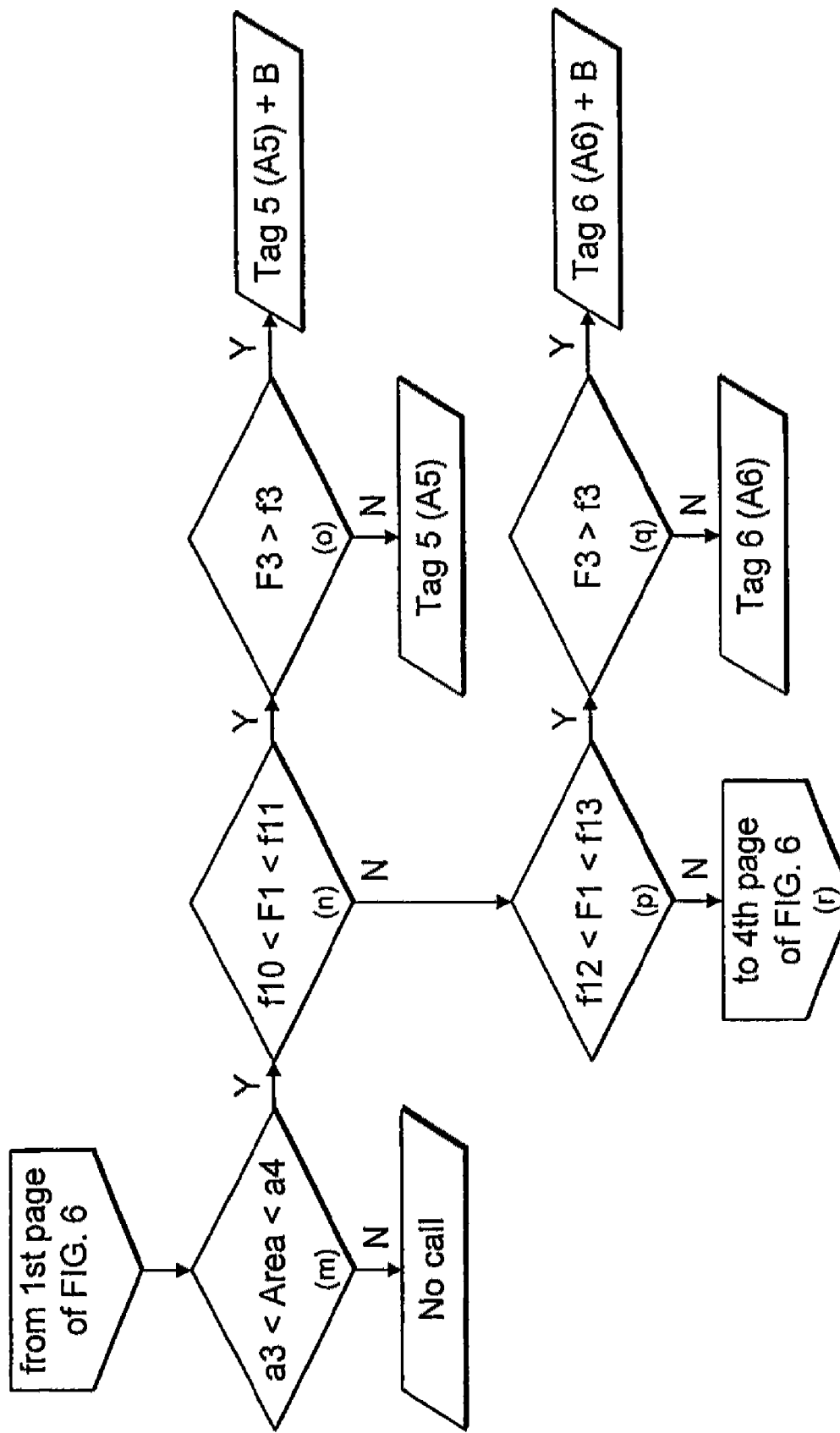
Figure 6:
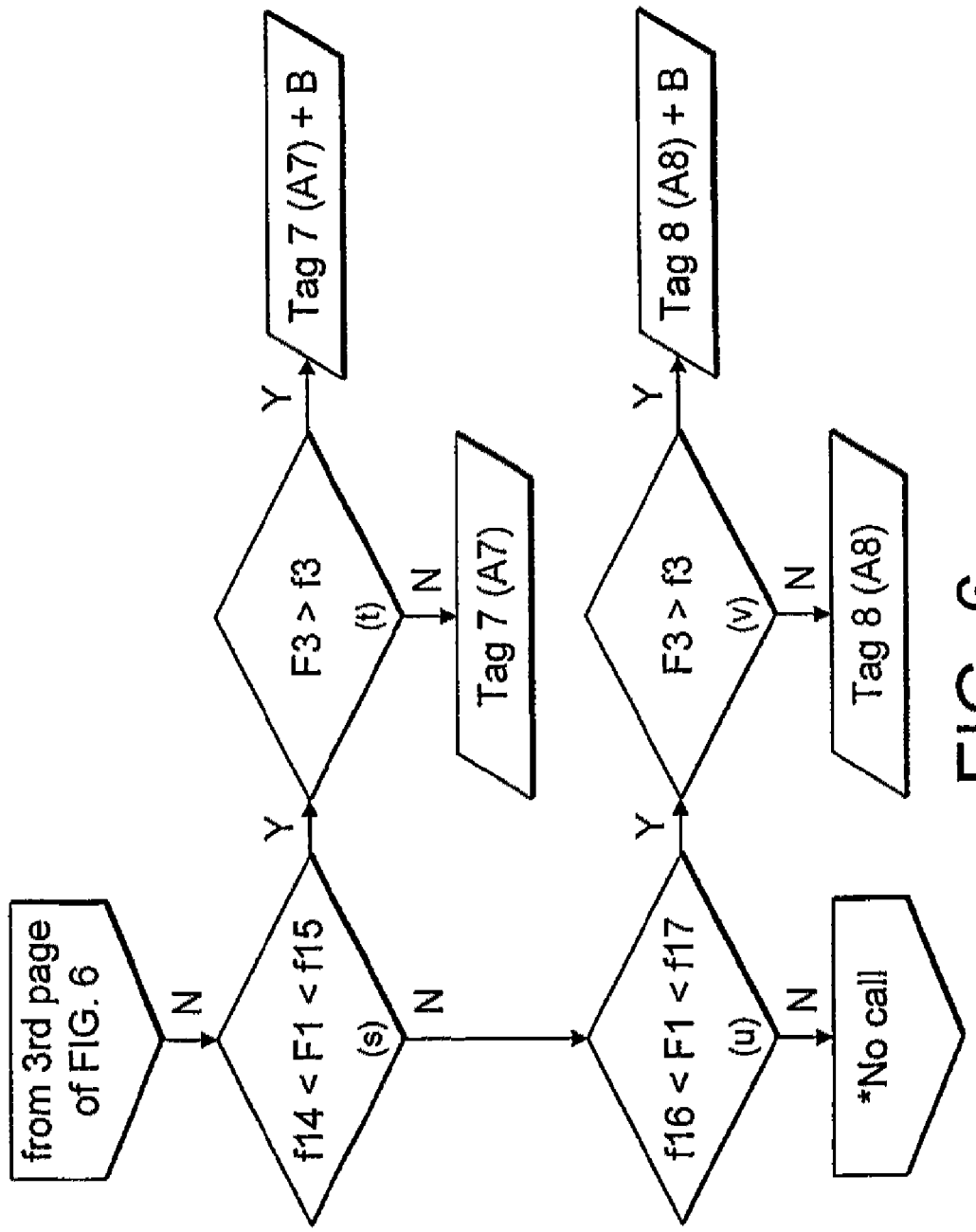
Figure 7:
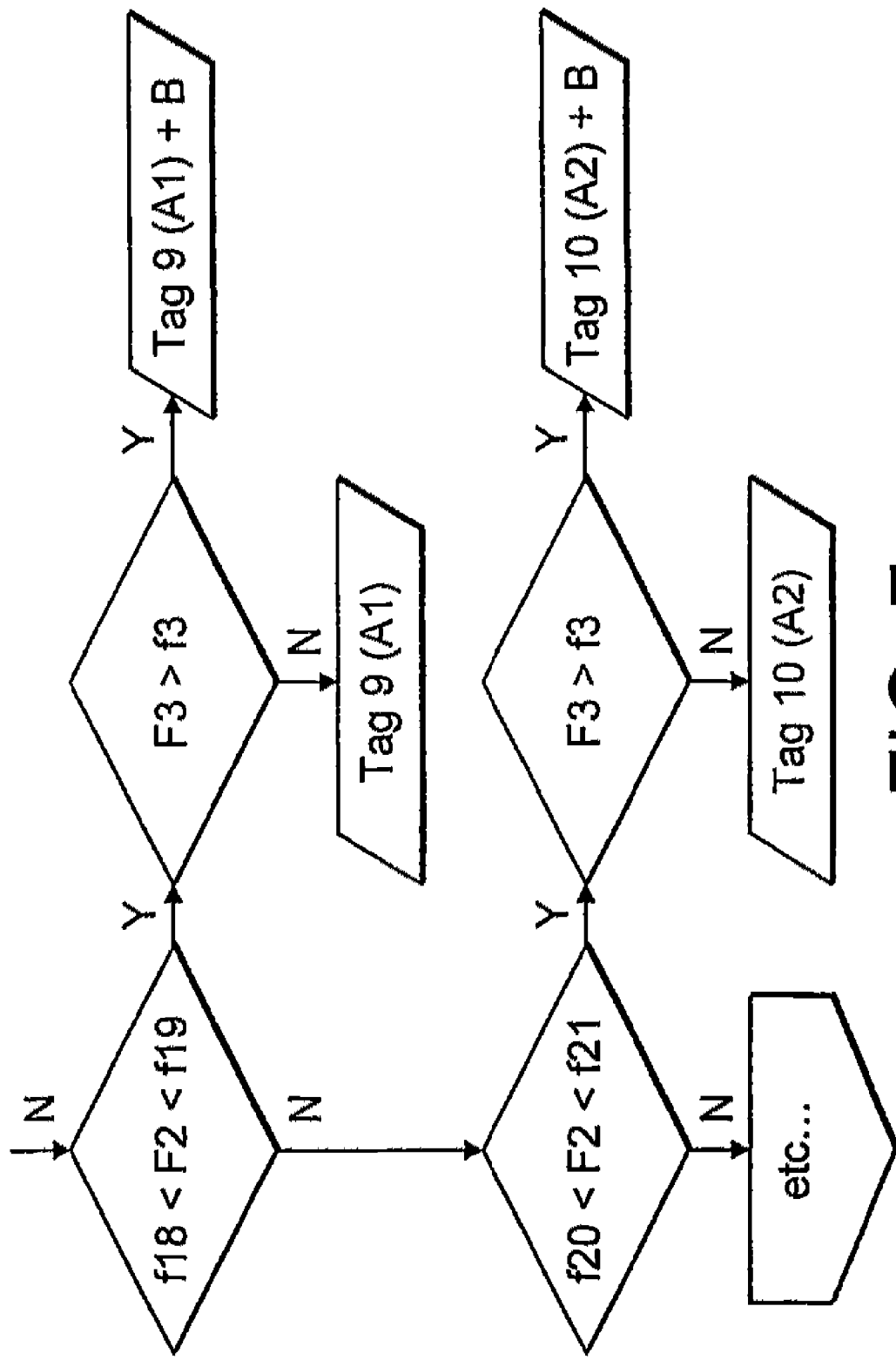

FIG. 7 shows an alternative flowchart in which one or more integers of a parameter are examined serially, such that the final 'No' decisions from FIG. 6 will go on to interrogate those integers for a further parameter. Fluorophore A is Starfire Red and Fluororophore B is TRITC. For example, F1 and F2 may be examined serially, such that the final 'No' decisions from FIG. 6 will go on to interrogate the Starfire Red values for the relevant size tag. F1—mean density measurement for UV2 channel; F2—mean density measurement for Starfire Red channel; F3—mean density measurement for TRITC channel; f18—lower limit for fluorescence of tag 9; f19—upper limit for fluorescence of tag 9; f3—lower threshold for TRITC fluorescence of all tags1; Y=yes; N=no.

Figure 8:
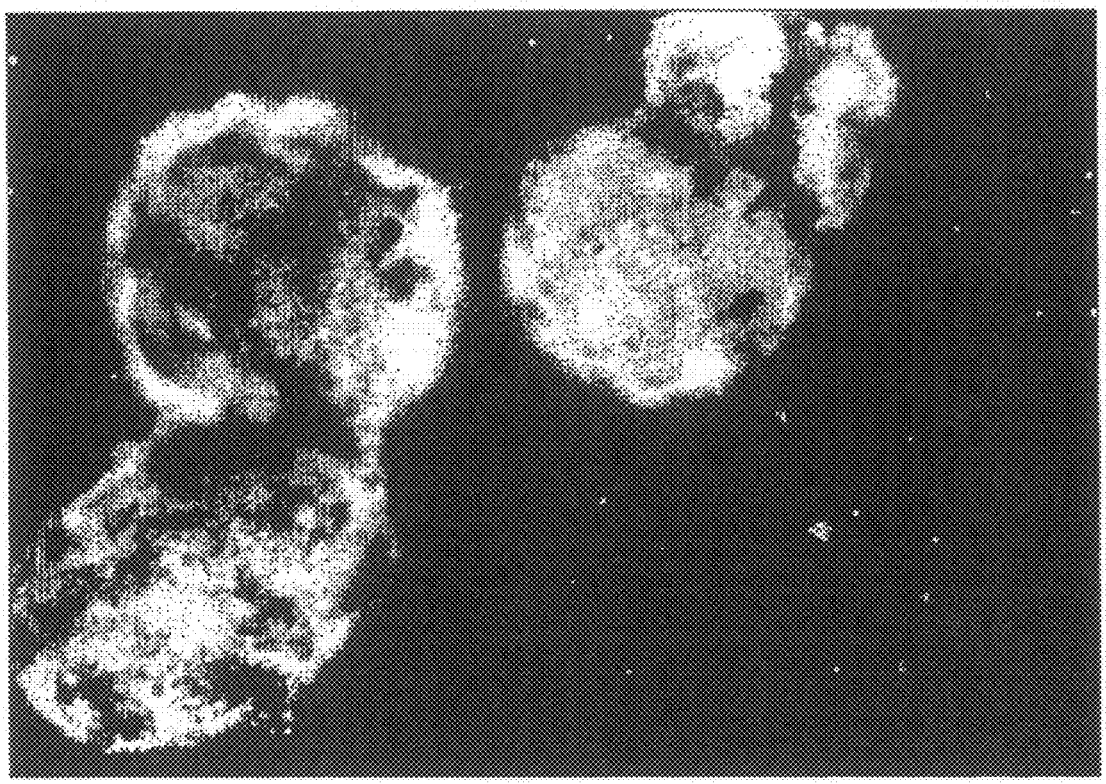

FIG. 8 shows a macroporous CULTISPHER-G gelatine microcarriers (Percell Biolytica AB) seeded with mouse ES cells and stained with a kit showing alkaline phosphatase activity, a marker of pluripotency.

Figure 9:
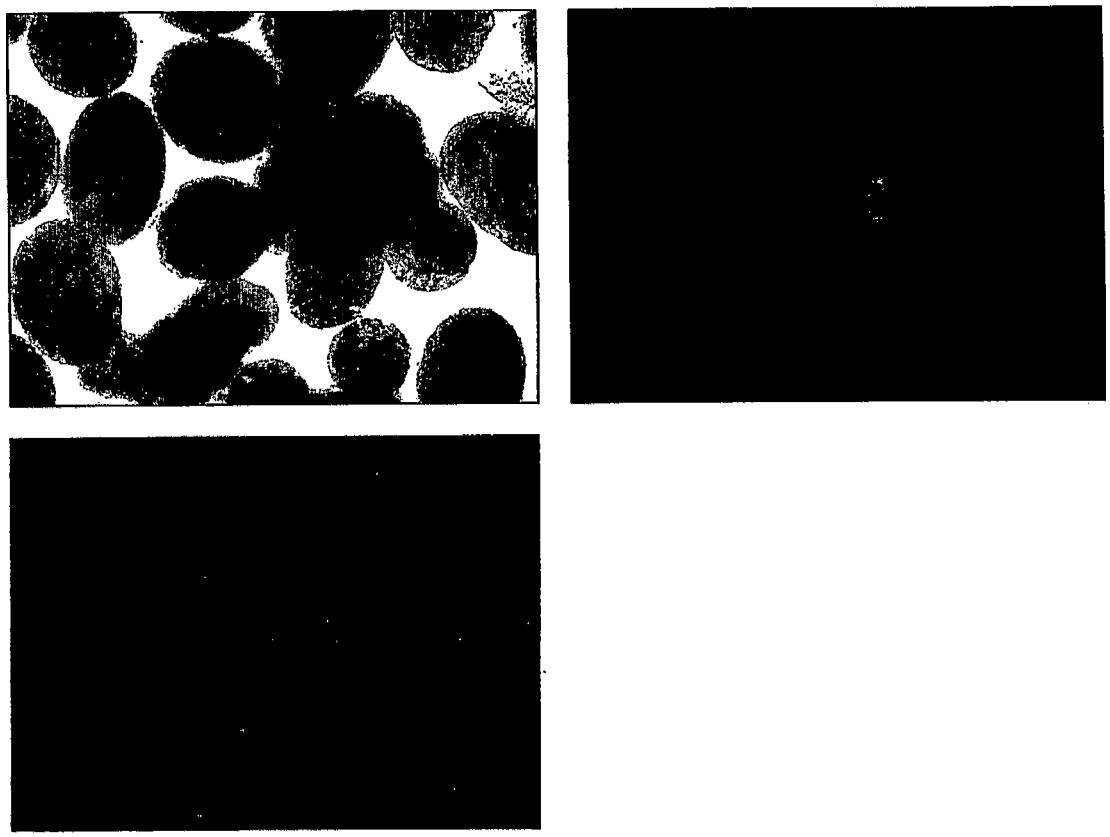

FIG. 9 shows a sample of the 140,000 microcarriers processed by Combinatorial Cell culture through the matrix shown in Table 1 and incubated on D13 with the macrophage assay reagent DQ-ovalbumin (Molecular Probes). Top left panel shows a phase contrast image of the microcarriers. The top right image shows the same field using a FITC filter set, whereby macrophages are easily distinguishable as large, round cells internally labelled with green fluorescence. The bottom left image shows the same field using a FITC filter set, revealing UV2-loaded tags associated with the microcarriers.

Figure 10:
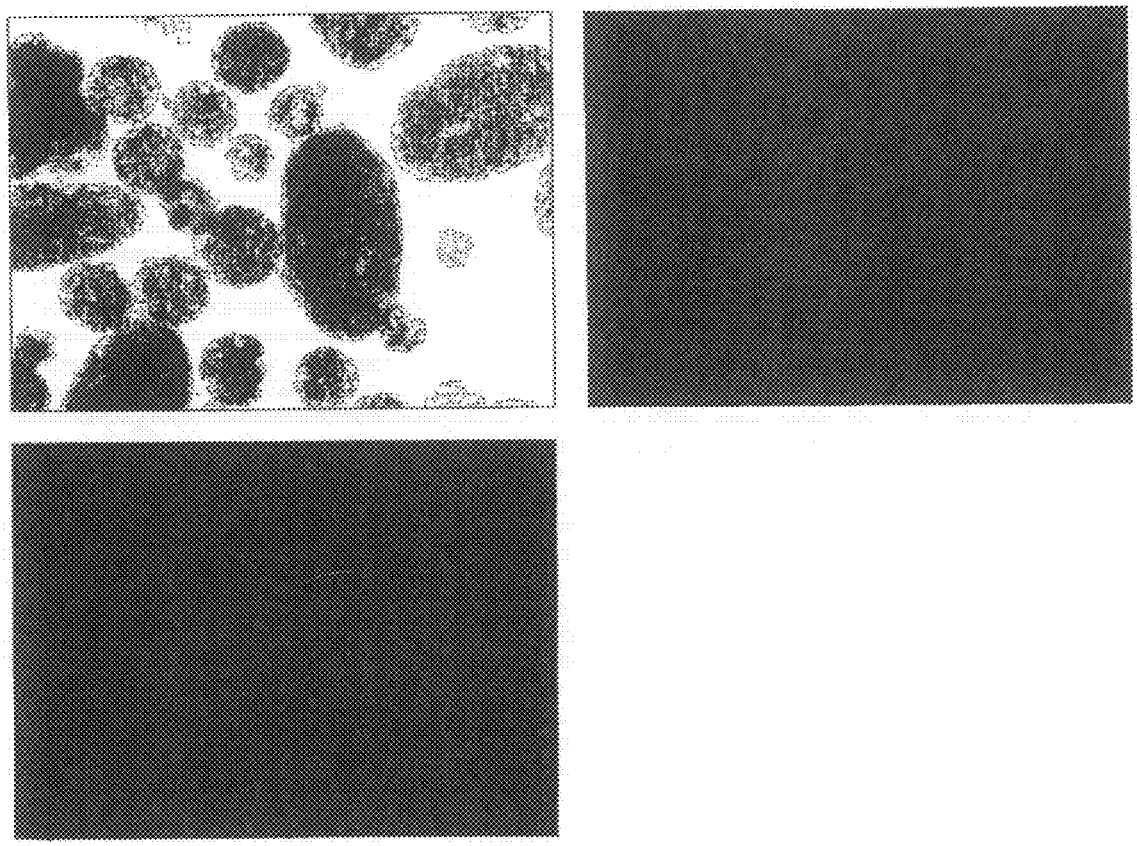

FIG. 10 is as for FIG. 9 but for a different field.

Figure 11:
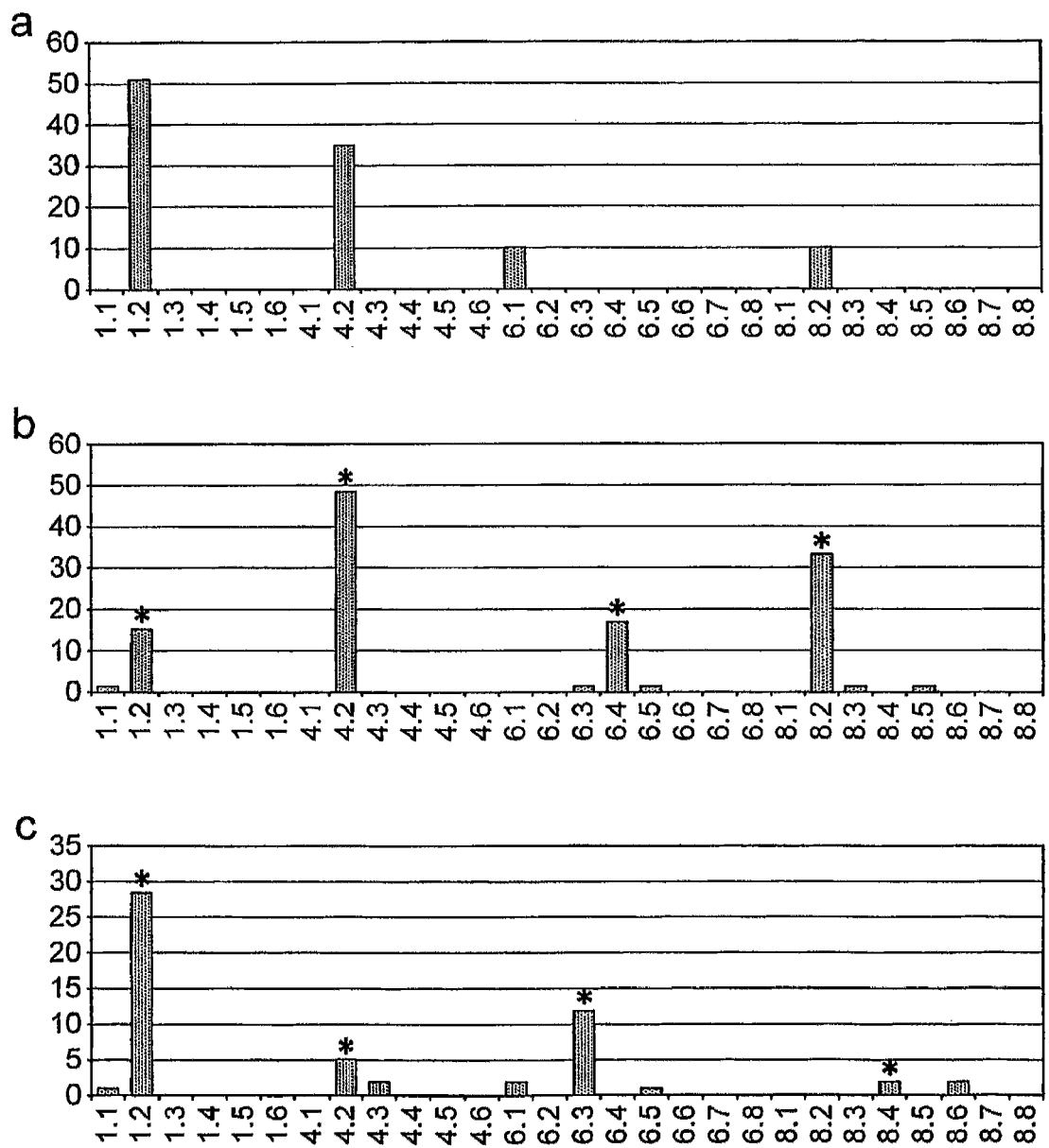

FIG. 11 represents graphs showing the number and identity of all tags found on the microphage-bearing microcarriers a) C5, b) A22 and c) E6. The bars marked with an asterisk in b) and c) denote the conditions which were later determined to result in reproducible macrophage differentiation.

Figure 12:
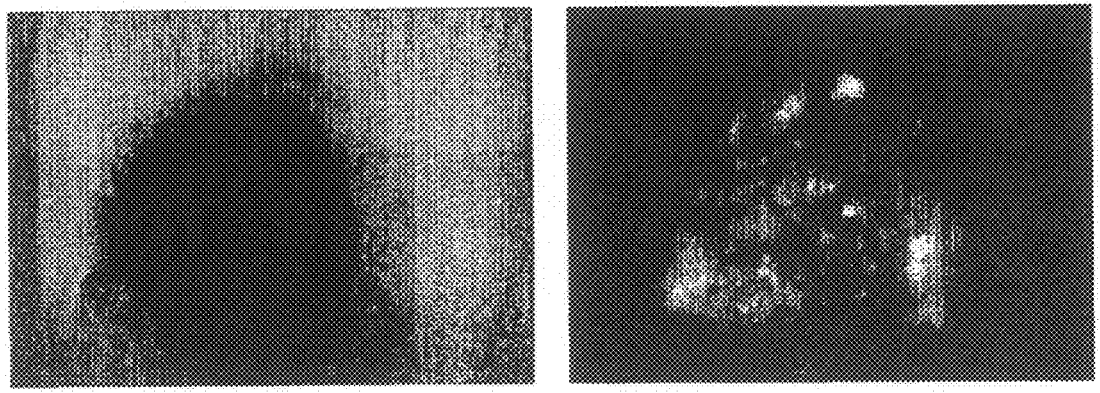

FIG. 12 is an example of a microcarrier bearing large number of macrophage stained with DQ-ovalbumin (Molecular Probes).

Figure 13:
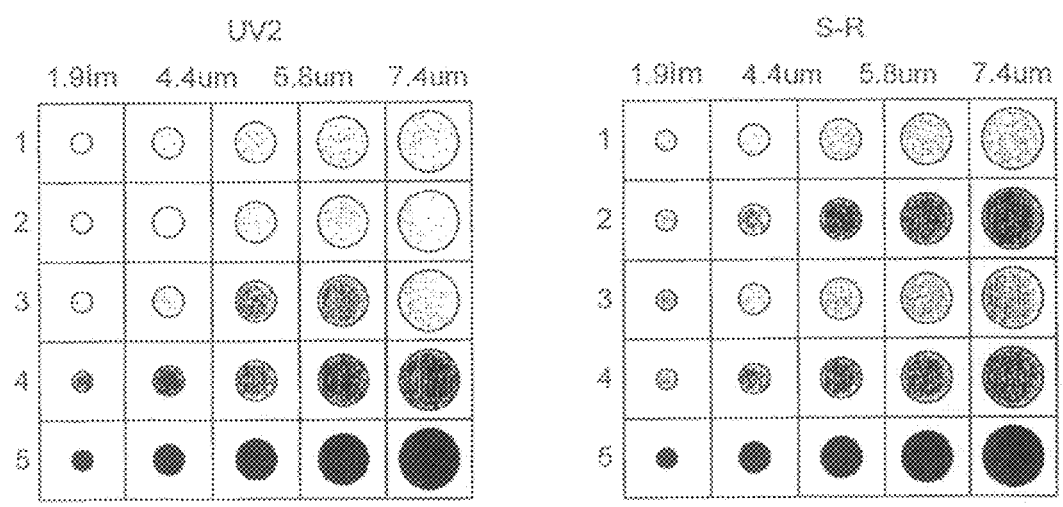

FIG. 13 is a graphical representation of the 50 microsphere tags commissioned from Bangs Laboratories (Fishers, Ind.). The microspheres were sized between 1.87 µm and 9.77 µm and were dyed with five distinguishable intensities of the fluorophore Starfire Red or alternatively UV2.

Figure 14:
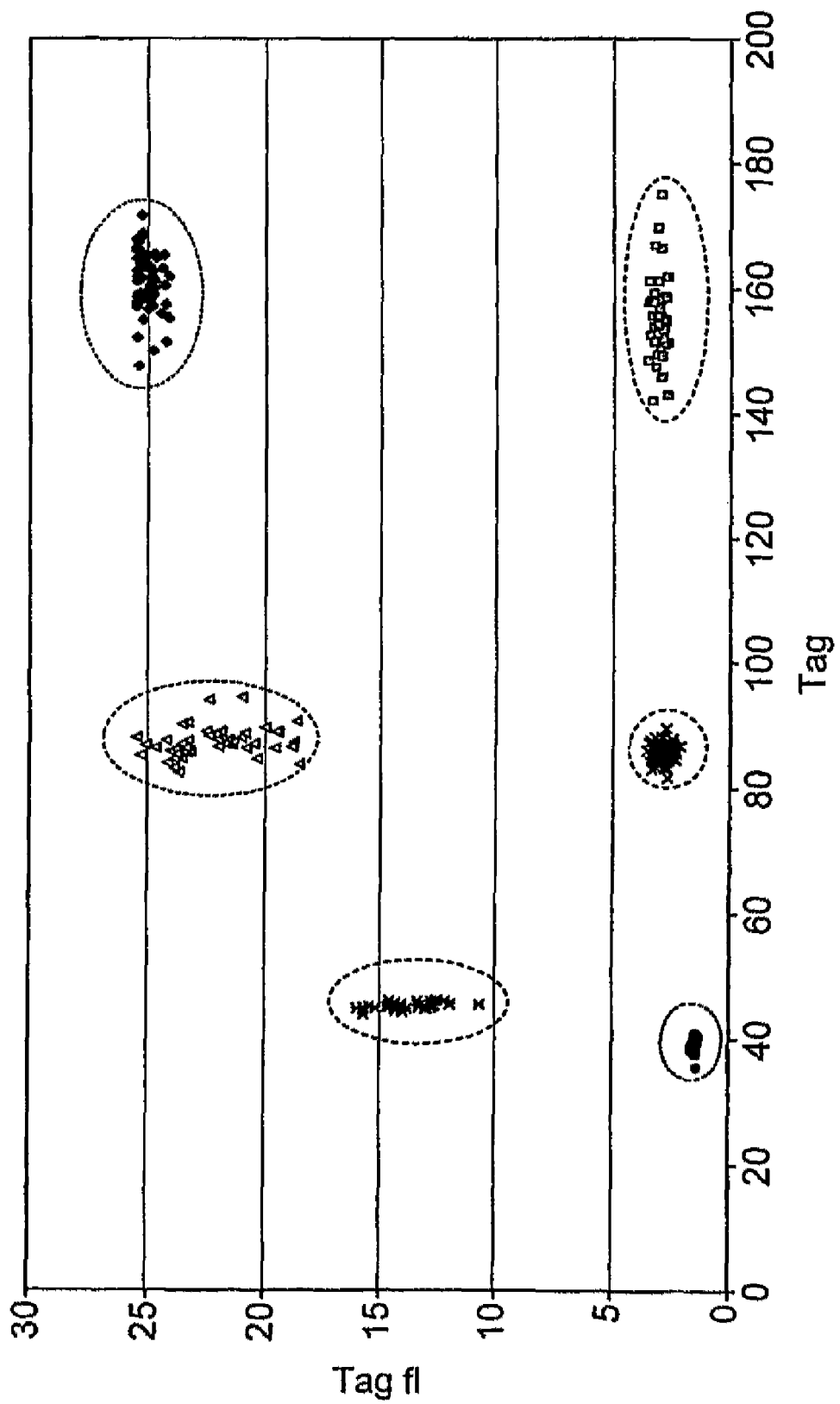

FIG. 14 is a calibration sample of Starfire Red dyed microsphere tags analysed according to tag size and fluorescence intensity at a given exposure setting. A similar calibration sample was used to determine parameters (denoted by ovals) for the classification of tags bound to microcarriers.

Figure 15:
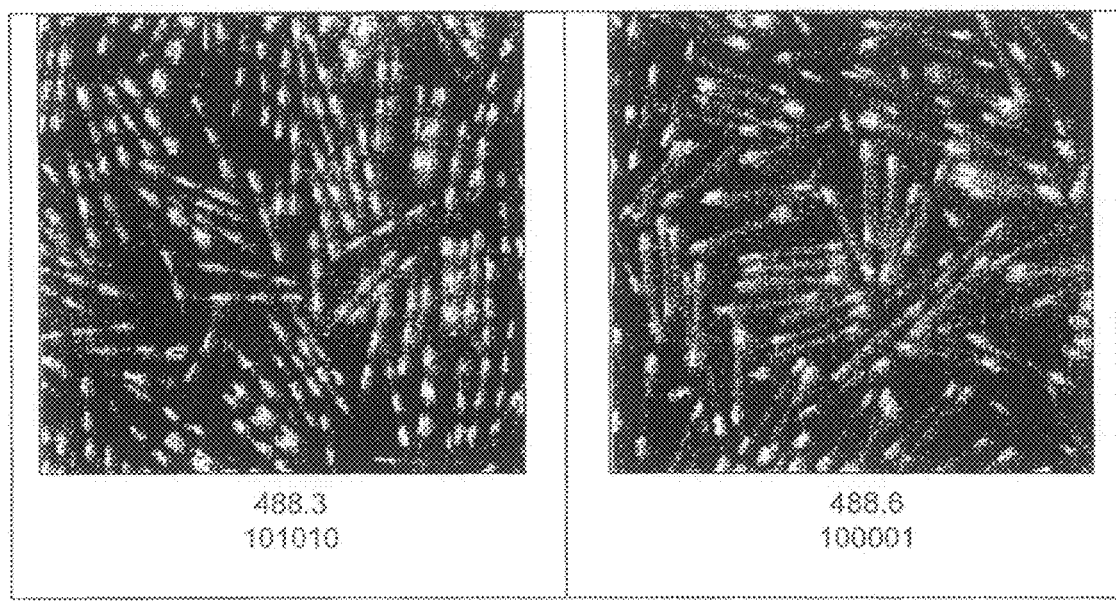

FIG. 15 shows quality control images of rod-shaped particles used in the experiment, obtained using illumination at 430 nm and a 63× objective. Left image 101010; Right image 100001 (where 1=Ag and 0=Au)

Figure 16:
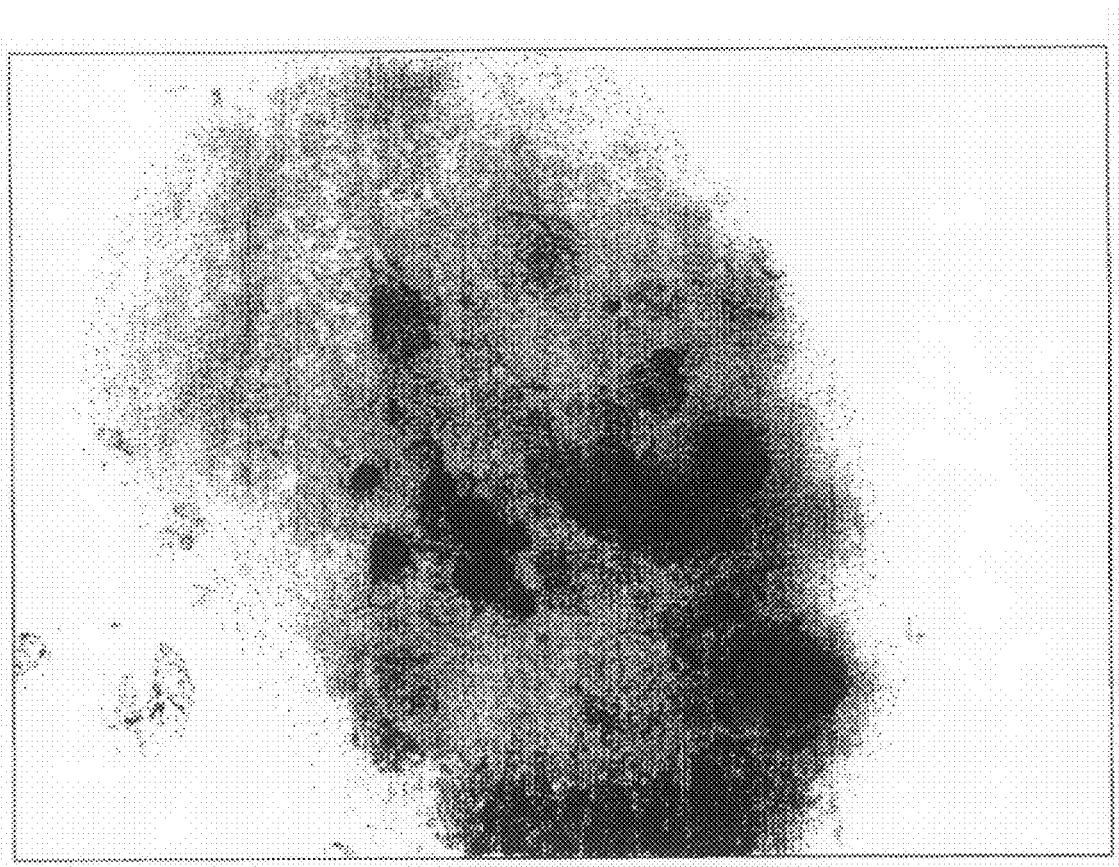

FIG. 16 is an image of a labelled cell unit stained with neutral red vital stain to reveal living cells and showing associated rod-shaped particles (indicated with arrows), obtained using bright field illumination and a 20× objective.

Figure 17:

FIG. 17 is an image of rod-shaped particles liberated following proteinase K digestion of a labelled cell unit, obtained using bright field illumination and a 20× objective.

Figure 18:
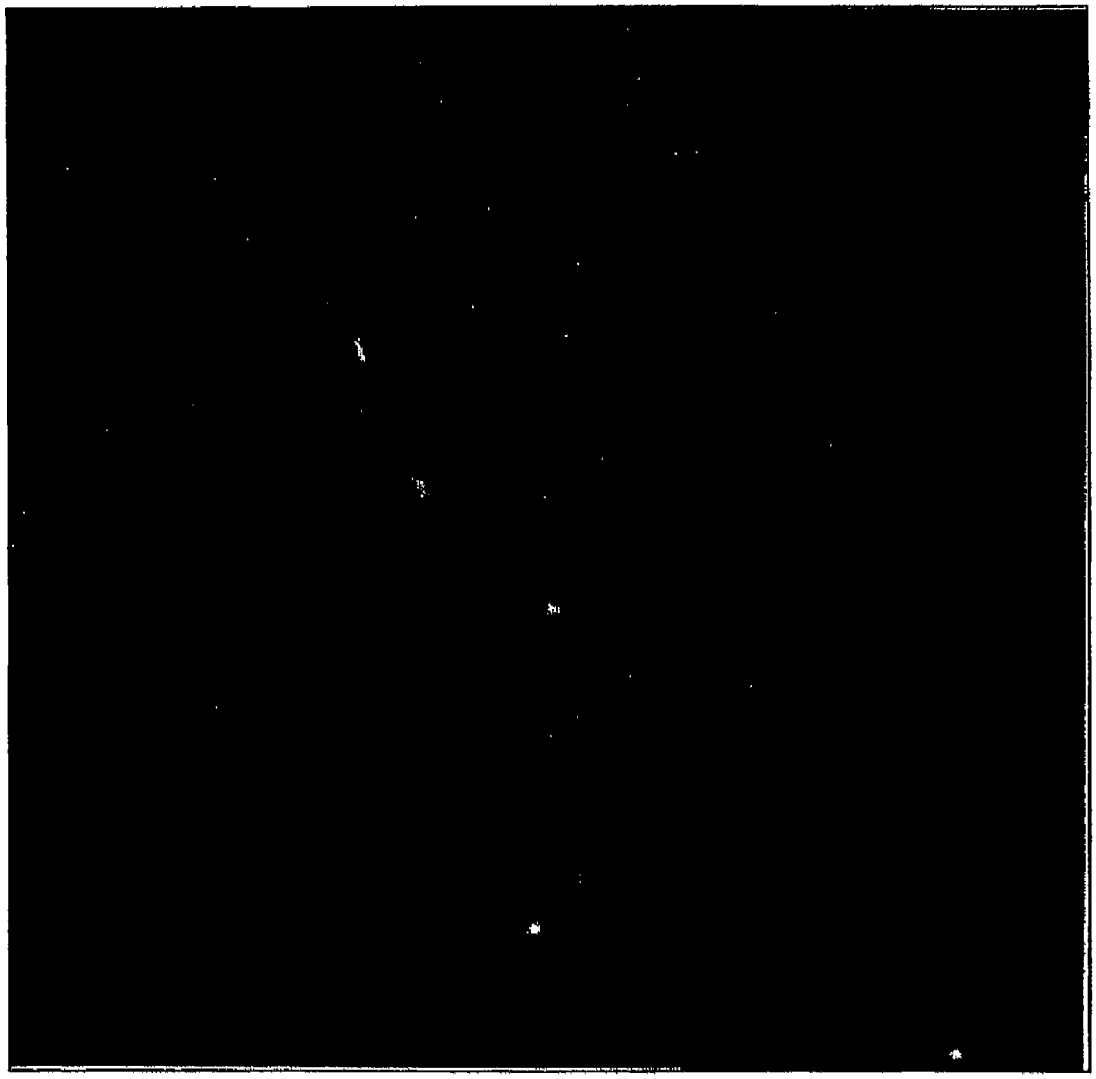

FIG. 18 is an image showing discrimination of two different particles liberated following proteinaseK digestion of a labelled cell unit, obtained using a CFP filter set (Ex. 436/10; Em. 465/30) with a 100× oil immersion objective. The particle on the left is 100001 and the particle on the right is 101010.

DETAILED DESCRIPTION OF THE INVENTION

Definitions

Culture Conditions As used herein, the term "culture conditions" refers to the environment which cells are placed in or are exposed to in order to promote growth or differentiation of said cells. Thus, the term refers to the medium, temperature, atmospheric conditions, substrate, stirring conditions and the like which may affect the growth and/or differentiation of cells. More particularly, the term refers to specific agents which may be incorporated into culture media and which may influence the growth and/or differentiation of cells.

Cell A cell, as referred to herein, is defined as the smallest structural unit of an organism that is capable of independent functioning, or a single-celled organism, consisting of one or more nuclei, cytoplasm, and various organelles, all surrounded by a semipermeable cell membrane or cell wall. The cell may be prokaryotic, eukaryotic or archaebacterial. For example, the cell may be a eukaryotic cell. Mammalian cells are preferred, especially human cells. Cells may be natural or modified, such as by genetic manipulation or passaging in culture, to achieve desired properties. A stem cell is defined in more detail below, and is a totipotent, pluripotent or multipotent cell capable of giving rise to more than one differentiated cell type. Stem cells may be differentiated in vitro to give rise to differentiated cells, which may themselves be multipotent, or may be terminally differentiated. Cells differentiated in vitro are cells which have been created artificially by exposing stem cells to one or more agents which promote cell differentiation.

Cellular process A cellular process is any characteristic, function, process, event, cause or effect, intracellular or extracellular, which occurs or is observed or which can be attributed to a cell. Examples of cellular processes include, but are not limited to, viability, senescence, death, pluripotency, morphology, signalling, binding, recognition, molecule production or destruction (degradation), mutation, protein folding, transcription, translation, catalysis, synaptic transmission, vesicular transport, organelle function, cell cycle, metabolism, proliferation, division, differentiation, phenotype, genotype, gene expression, or the control of these processes.

Cell unit A group of cells, which may be a group of one. Pools of cell units may be sorted, subdivided and handled without substantially dissociating the cell units themselves, such that the cell unit behaves as a colony of cells and each cell in the cell unit is exposed to the same culture conditions. For some embodiments, a cell unit may comprise a microcarrier or bead to which is adhered a group of cells.

Totipotent A totipotent cell is a cell with the potential to differentiate into any type of somatic or germ cell found in the organism. Thus, any desired cell may be derived, by some means, from a totipotent cell.

Pluripotent A pluripotent cell is a cell which may differentiate into more than one, but not all, cell types.

Tag In one aspect, the term "tag", as used herein, refers to any tag that is used to identify a cell unit and/or determine a culture condition, or a sequence of culture conditions, to which the cell unit has been exposed. In another aspect, the term "tag" refers to any tag that is added to a cell unit as a means of specifically labelling that cell unit, thus facilitating the identification of a cell unit and/or the determination of a culture condition and/or a sequence of culture conditions, to which the cell unit has been exposed. Suitably, the tag exists in a number of related but distinct variants which are easily distinguishable, as described in further detail herein. The tag typically forms part of a complex with a microcarrier—such as a CULTISPHER-G microcarrier or a CYTOPORE 2 microcarrier. For some embodiments, the tag is a sphere or a bead—such as a microsphere or a microbead. For some embodiments the tag is a rod-shaped particle—such as a nanowire. As referred to herein, the term "tag" is synonymous with the term "label".

Exposure to culture conditions A cell is exposed to culture conditions when it is placed in contact with a medium, or grown under conditions which affect one or more cellular process(es) such as the growth, differentiation, or metabolic state of the cell. Thus, if the culture conditions comprise culturing the cell in a medium, the cell is placed in the medium for a sufficient period of time for it to have an effect. Likewise, if the conditions are temperature conditions, the cells are cultured at the desired temperature.

Pooling The pooling of one or more groups of cell units involves the admixture of the groups to create a single group or pool which comprises cell units of more than one background, that is, that have been exposed to more than one different sets of culture conditions. A pool may be subdivided further into groups, either randomly or non-randomly; such groups are not themselves "pools" for the present purposes, but may themselves be pooled by combination, for example after exposure to different sets of culture conditions.

Proliferation Cell growth and cell proliferation are used interchangeably herein to denote multiplication of cell numbers without differentiation into different cell types or lineages. In other words, the terms denote increase of viable cell numbers. In some embodiments, proliferation is not accompanied by appreciable changes in phenotype or genotype.

Differentiation Cell differentiation is the development, from a cell type, of a different cell type. For example, a bipotent, pluripotent or totipotent cell may differentiate into a neural cell. Differentiation may be accompanied by proliferation, or may be independent thereof. The term 'differentiation' generally refers to the acquisition of a phenotype of a mature cell type from a less developmentally defined cell type, e.g. a neuron, or a lymphocyte, but does not preclude transdifferentiation, whereby one mature cell type may convert to another mature cell type e.g. a neuron to a lymphocyte.

Differentiation state The differentiation state of a cell is the level to which a cell has differentiated along a particular pathway or lineage.

State of a cellular process The state of a cellular process refers to whether a cellular process is occurring or not and in complex cellular processes can denote a particular step or stage in that cellular process. For example, a cellular differentiation pathway in a cell may be inactive or may have been induced and may comprise a number of discrete steps or components such as signalling events characterised by the presence of a characteristic set of enzymes or intermediates.

Gene A gene is a nucleic acid which encodes a gene product, be it a polypeptide or an RNA gene product. As used herein, a gene includes at least the coding sequence which encodes the gene product; it may, optionally, include one or more regulatory regions necessary for the transcription and/or translation of the coding sequence.

Gene Product A gene product is typically a protein encoded by a gene in the conventional manner. However, the term also encompasses non-polypeptide gene products, such as ribonucleic acids, which are encoded by the gene.

Nucleic acid synthesis Nucleic acids may be synthesised according to any available technique. In some embodiments, nucleic acid synthesis is automated. Moreover, nucleic acids may be produced by biological replication, such as by cloning and replication in bacterial or eukaryotic cells, according to procedures known in the art.

Differential Expression Genes which are expressed at different levels in response to cell culture conditions can be identified by gene expression analysis, such as on a gene array, by methods known in the art. Genes which are differentially expressed display a greater or lesser quantity of mRNA or gene product in the cell under the test conditions than under alternative conditions, relative to overall gene expression levels.

Transfection Genes may be transfected into cells by any appropriate means. The term is used herein to signify conventional transfection, for example using calcium phosphate, but also to include other techniques for transferring nucleic acids into a cell, including transformation, viral transduction, electroporation and the like.

Modulation The term modulation is used to signify an increase and/or decrease in the parameter being modulated. Thus, modulation of gene expression includes both increasing gene expression and decreasing gene expression.

Integer This term refers to an individual entity of a parameter. By way of example, if the parameter is the size of a tag, then the integer will be one or more of specific sizes within the parameter.

Identifying Tags Associated with One or More Cell Units

In one aspect, there is provided a method for determining the cell culture history of a cell unit labelled with more than one tag (e.g. more than one type of tag) comprising the steps of: (a) measuring one or more parameters of each tag that is used to label the cell unit; (b) identifying each tag in the cell unit; and (c) correlating the identity of each tag to the identity of the cell unit and/the specific cell culture conditions to which the cell unit has been exposed.

In a further aspect, there is also provided a method for determining the cell culture history of a cell unit labelled with one or more types of tag comprising the steps of: (a) obtaining the tags from the cell units in a form suitable for analysis; (b) measuring one or more parameters of each tag that is used to label a cell unit; (c) identifying each tag in the cell unit; and (d) correlating the identity of each tag to the chronology and identity of the cell culture conditions to which the cell unit has been exposed.

The parameter(s) may be the size of the tags and/or the optical properties of the tags. Examples of the optical properties of the tags include, but are not limited to, light reflectivity, colour, the fluorescence emission wavelength(s) and/or the fluorescence emission intensity.

The cell unit(s) to be analysed may be separated from a sample that may contain many different cell units.

The tags in a cell unit(s) of interest may be isolated from the cell unit. In some embodiments, this is achieved by enzymatic digestion and/or acid hydrolysis of the cell unit. In some embodiments, this is achieved using the methods described herein. Advantageously, in certain embodiments this results in destruction of the cell unit but the tags are obtained intact.

In one embodiment of the present invention, one or more different tags are measured for a cell unit—such as a cell unit contained in a sample comprising a plurality of cell units.

In some embodiments, there will be from about 2 to about 50 or more different (types of) tags per cell unit. In some embodiments there will be from about 2 to about 40 different (types of) tags per cell unit. In some embodiments there will be from about 2 to about 30 different (types of) tags per cell unit. In some embodiments there will be from about 2 to about 20 different (types of) tags per cell unit. In some embodiments there will be from about 2 to about 10 different (types of) tags per cell unit.

In some embodiments, there will be from about 5 to about 50 or more different (types of) tags per cell unit. In some embodiments, there will be from about 10 to about 50 or more different (types of) tags per cell unit. In some embodiments, there will be from about 15 to about 50 or more different (types of) tags per cell unit. In some embodiments, there will be from about 20 to about 50 or more different (types of) tags per cell unit. In some embodiments, there will be from about 25 to about 50 or more different (types of) tags per cell unit. In some embodiments, there will be from about 30 to about 50 or more different (types of) tags per cell unit. In some embodiments, there will be from about 35 to about 50 or more different (types of) tags per cell unit. In some embodiments, there will be from about 40 to about 50 or more different (types of) tags per cell unit. In some embodiments, there will be from about 45 to about 50 or more different (types of) tags per cell unit. In some embodiments, it is expected that there will be about 50 or more different (types of) tags per cell unit.

In some embodiments, there will be about 55, 60, 65, 70, 75 or even 80 or more different (types of) tags per cell unit. In some embodiments, there will be about 55, 60, 65, 70, 75 or even 80, 90, 100, 250, 500, 750, or 1000 or more different (types of) tags per cell unit.

Each of the parameters described above may have a number of different integers. In some embodiments, there are at least 2, 3, 4 or 5 different integers for each parameter. In some embodiments, there are at least 10 different integers for each parameter. In some embodiments, there are at least 15 different integers for each parameter. In some embodiments, there are at least 20 different integers for each parameter. In some embodiments, there are at least 25 different integers for each parameter. In some embodiments, there are at least 30 different integers for each parameter. In some embodiments, there are at least 35 different integers for each parameter. In some embodiments, there are at least 40 different integers for each parameter. In some embodiments, there are at least 45 different integers for each parameter. In some embodiments, there are at least 50 different integers for each parameter.

In some embodiments, there are at least 2 different parameters and more than 5 different integers for each parameter.

In some embodiments, there are at least 2 different parameters and more than 5 and less than 50 different integers for each parameter. In some embodiments, there are at least 2 different parameters and 50 or less different integers for each parameter. In some embodiments, there are at least 2 different parameters and 50 or more different integers for each parameter. In some embodiments, there are at least 2 different parameters and 40 or less different integers for each parameter. In some embodiments, there are at least 2 different parameters and 30 or less different integers for each parameter. In some embodiments, there are at least 2 different parameters and 20 or less different integers for each parameter. In some embodiments, there are at least 2 different parameters and 10 or less different integers for each parameter.

Each cell unit may contain more than one (e.g. multiple) tags of each species.

Advantageously, this method can be automated such that many cell units and/or many samples can be processed. This is particularly advantageous, since each sample may have many (e.g. hundreds) of different tags in it, thereby generating a large amount of data.

For some embodiments of the present invention, there is a maximum of 50 different tags. By way of example, using the CML hydrophilic microbeads as described herein will typically result in this number of microbeads. The CML hydrophilic microbeads may be used together with one or more microcarriers. In some embodiments, the CML hydrophilic microbeads are used together with a CYTOPORE 2 microcarrier.

The tags in the sample may all be different or they may all be the same. The tags may be of different sizes—such as between about 1-10 µm, preferably about 1.9 µm, about 4.4 µm, about 5.4 µm, about 5.8 µm, about 7.4 µm, about 9.7 µm and/or about 9.8 µm. The tags may be microspheres—such as CML microspheres—and the diameters of such microspheres may be between 1-10 µm, preferably about 1.9 µm, about 4.4 µm, about 5.4 µm, about 5.8 µm, about 7.4 µm, about 9.7 µm and about 9.8 µm.

For some embodiments, there is a maximum of 1000 different tags. By way of example, using the rod-shaped nanowires striped with silver and gold as described herein can result in this number of tags. The said nanowires may be used together with one or more microcarriers. In some embodiments, the nanowires are used together with a CULTI-SPHER-G microcarrier.

In one embodiment, a particular tag is correlated with a known cell culture condition. Accordingly, once the cell unit has been labelled with this tag and has been cultured in the corresponding conditions, it is possible to identify or select those culture conditions that have given rise to a particular cell unit of interest.

Whilst various methods of image analysis are available in the art, a combination of Image Pro Plus imaging software by Media Cybernetics, a Nikon TE2000-S fluorescence microscope and an Evolution VF cooled monochrome camera, supplied by Media Cybernetics may be used.

In one embodiment one or more image(s) of each tag in the cell unit in the field of interest is measured. Typically, this may be achieved using microscopy—such as bright field microscopy, phase-contrast microscopy, oblique illumination microscopy, dark field microscopy, differential interference contrast microscopy, reflection contrast microscopy, varel contrast microscopy, polarizing microscopy, interference microscopy and fluorescence microscopy. Suitably, outlines may be drawn for the one or more image(s) of each tag in the cell unit in the field of interest and/or one or more fluorescence image(s) of each tag in the cell unit in the field of interest is measured. The fluorophore may emit, for example, a blue, green, near red or far red fluorescence. Suitably, the fluorophore is selected from the group consisting of UV2, Starfire Red and TRITC. The quantity of fluorophore may be selected from 5 different ranges (e.g. ranges of fluorescence intensity) and each different range is discrete. In some embodiments, the ranges may differ by about 2 to 5-fold or more in brightness. In some embodiments, the ranges may differ by about 5 to 10-fold or more in brightness. In some embodiments, the ranges may differ by about 2 to 100-fold or more in brightness. In some embodiments, the ranges may differ by about 2 to 1000-fold or more in brightness. In some embodiments, the ranges may differ by about 2, 5, 10, 100 or 1000-fold or more in brightness.

Suitably, the outlines for the one or more image(s) are loaded onto the one or more fluorescence image(s) and one or more fluorescence image(s) of each tag in the cell unit in the field of interest may be measured for each fluorophore that is used to label the tags. Each tag in the cell unit may be identified by reading the one or more parameters—such as the area and/or optical density—of the tag within the one or more outlines.

Thus, by way of example, tags may be analysed by microscopy using a Nikon TE2000-S inverted epifluorescent microscope equipped with filter sets for visualization of the fluorophores—such as TRITC, DAPI (UV2), GFP-B (all from Nikon) and Cy5 (Chroma Technology). Images may be captured using an Evolution VF cooled monochrome camera and image analysis performed using Image Pro Plus (both from Media Cybernetics).

The outlines of single microspheres are typically captured using microscopy methods and the areas within these calculated to size the tags. The fluorescence intensities in the different channels may be used to further specify the identity of each tag by comparison to reference samples containing known tags.

Suitably, the microscopy methods is selected fro the group consisting of bright field microscopy, phase-contrast microscopy, oblique illumination microscopy, dark field microscopy, differential interference contrast microscopy, reflection contrast microscopy, varel contrast microscopy, polarizing microscopy, interference microscopy and fluorescence microscopy.

In one embodiment, the microscopy method is bright field microscopy.

Optionally, the data that is obtained may be processed using further methods described herein, that provide for the chronology and identity of cell culture conditions to which a cell unit in a sample has been exposed to be determined. Advantageously, this process may be automated thereby allowing a large amount of data to be rapidly processed.

Advantageously, the process utilises software that counts the number of each type of tag and then outputs this data in the form of a list, a graph or a chart.

Advantageously, the data may be inputted into a spreadsheet for high throughput analysis.

In one aspect, the method of analysing this data comprises a first step of comparing the upper and lower limits of at least one parameter of a tag with the mean measurement of the at least one parameter of the tag. In one embodiment of the present invention, the upper and lower limits of any parameter are obtained or obtainable by analysing a plurality of reference tags of the same species. If the lower limit is less than the mean measurement and the upper limit is higher than the mean measurement then the method compares the upper and lower limits of a second parameter of a tag with the mean measurement of the second parameter of the tag. If the lower limit of the second parameter is less than the mean measurement for that parameter and the upper limit of the second parameter is higher than the mean measurement of that parameter then the method compares one or more further parameters relative to a lower limit of the corresponding parameter.

If at any point the mean measurement of any parameter does not fall between the upper and lower limits determined for that parameter then the method compares that mean measurement relative to a second range comprising different limits for that same parameter.

In one aspect, there is provided a method for determining the chronology and identity of the cell culture conditions to which a cell unit has been exposed comprising the step of: comparing the upper and lower limits of at least one parameter of a tag with the mean measurement of the at least one parameter of the tag.

In a further aspect, there is provided a method for determining the chronology and identity of the cell culture conditions to which a cell unit has been exposed comprising the steps of: (a) comparing the upper and lower limits of at least one parameter of a tag with the mean measurement of the at least one parameter of the tag; (b) comparing the mean measurement for the at least one parameter of the tag with the lowest limit for the at least one parameter of the tag; and (c) correlating the measurement of the at least one parameter of the tag with the identity of the tag associated with the cell unit.

In one embodiment, if the lower limit is less than the mean measurement and the upper limit is higher than the mean measurement then the method compares the upper and lower limits of a second parameter of a tag with the mean measurement of the second parameter of the tag. For example, the first parameter may be size and the second parameter may be the intensity or level of fluorescence.

In one embodiment, if the lower limit of the second parameter is less than the mean measurement for that parameter and the upper limit of the second parameter is higher than the mean measurement of that parameter then the method compares one or more further parameters relative to a lower limit of the corresponding parameter.

In one embodiment, if the lower limit is not less than the mean measurement and the mean measurement is not less then than the upper limit then the upper and lower limits of at least one further integer of the same parameter of the tag is measured. By way of example, the further integer may include, but is not limited to a different size, a different fluorophore or a different range of fluorescence intensity. Accordingly, the parameter for each of these integers will be size, type of fluorophore and intensity of fluorescence, respectively.

In one embodiment, if the lower limit is less than the mean measurement and the mean measurement is less then than the upper limit then the at least one further parameter for the tag is measured—such as the size, type of fluorophore and/or level of fluorophore of the tag.

In one embodiment, if the mean measurement for the at least one parameter of the tag is greater than the lowest limit for at least one parameter of the tag, then the result is correlated with one or more tags that possess the one or more parameters.

In one embodiment, if the mean measurement for the at least one parameter of the tag is not greater than the lowest limit for the one or more parameters of the tag, then the result is correlated with a tag that possess the parameter.

In one embodiment, if the lower limit is not less than the mean measurement and the mean measurement is not less then than the upper limit for the at least one further parameter then the upper and lower limits of at least one further integer of the same parameter of the tag is measured.

In one embodiment, the method may be repeated for one or more further integers of the same parameter of the tag. In another embodiment, the method may even be repeated for all integers of the same parameter of the tag.

In one embodiment, if the lower limit is less than the mean measurement and the mean measurement is less then than the upper limit for the at least one further parameter and the mean measurement for the at least one parameter of the tag is greater than the lowest limit for at least one parameter of the tag, then the result is correlated with one or more tags that possess the one or more parameters.

In one embodiment, if the lower limit is less than the mean measurement and the mean measurement is less then than the upper limit for the at least one further parameter and the mean measurement for the at least one parameter of the tag is not greater than the lowest limit for the one or more parameters of the tag, then the result is correlated with a tag that possess the parameter.

In one embodiment, if the measurement of the at least one parameter of the tag cannot be correlated with the identity of the tag associated with the cell unit, then the method may comprises the additional steps of, for example, examining fluorophores serially, such that the final 'No' decisions from will go on to interrogate the fluorophores values for the relevant size tag, Suitably, the methods described herein are performed using one or more of the complexes described herein.

In a further aspect, there is provided a method for identifying one or more area and/or density values for a tag comprising the steps of: (a) obtaining one or more images of a tag that is used to label a cell unit; (b) drawing outlines for the one or more images of the tag; (c) loading the outlines for the one or more images of the tag; and (d) reading the area and/or density within the one or more outlines.

In one embodiment, the image may be a phase image.

Determination of the Identity or Cell Culture History of a Cell Unit

As already described above, when handling large numbers of cell units, their identity and/or cell culture history (for example the chronology and the exact nature of a series of culture conditions that any one group or unit may have been exposed to) can become confused. For instance, the split-pool protocol of cell culture necessarily involves mixing cell units in each round, making it difficult to follow individual units. Determining the cell culture history of a cell unit in a mixture of cell units, which have been subjected to multiple culture conditions, is sometimes referred to as 'deconvolution' of the cell culture history.

One method of determining the cell culture history of a cell unit in a mixture of cell units, is to label cell units and it is therefore advantageous to label the cell units. As described herein, tags—such as rod-shaped particles, microbeads and/ or microspheres may be used as labels or tags which are conjugated to a microcarrier—such as a cell-associated microcarrier. Subsequent detection and identification provides for a record of the chronology and identity of the cell culture conditions to which the cell unit has been exposed.

Microcarriers

A variety of microcarriers are available, ranging in shape and size and made of different materials.

By way of example, the microcarrier may be a porous microcarrier selected from the group consisting of CYTOPORE microcarrier (e.g. a CYTOPORE 1 microcarrier or a CYTOPORE 2 microcarrier), a CULTISPHER microcarrier, a CULTISPHER-G microcarrier, a CULTISPHER-GL microcarrier and a CULTISPHER-S microcarrier, an INFORMATRIX microcarrier, a MICROSPHERE microcarrier, a SIRAN microcarrier, and a MICROPOROUS MC microcarrier.

By way of further example, the microcarrier may be a solid microcarrier—such as a CYTODEX microcarrier (e.g. a CYTODEX 1, CYTODEX 2 or CYTODEX 3 microcarrier) a BIOSILON microcarrier, a BIOGLASS microcarrier, a FACT III microcarrier or a DE 52/53 microcarrier.

Microcarrier culture has significant advantages, including the scale-up of cultures, and also allows units of cells to be exposed to selected culture conditions as required in order to obtain the desired growth and/or differentiation conditions.

The surfaces of the microcarriers may be further modified by physical or chemical treatments, such as adsorption or covalent cross-linking of molecular entities with a desired charge or other desired characteristic.

In a broad embodiment, therefore, the invention provides a method for culturing cells in vitro, comprising growing said cells adhered to the microcarrier complexes described herein.

In one aspect, there is provided a complex comprising a microcarrier and a charged (e.g. negatively charged) tag. In other words, there is provided a microcarrier conjugated or labelled with a charged (e.g. negatively charged) microsphere.

In a further aspect, there is provided a microcarrier and a rod-shaped tag. In other words, there is provided a microcarrier conjugated or labelled with a rod-shaped tag.

CULTISPHER Microcarriers

CULTISPHER is manufactured from pharmaceutical grade porcine gelatin via a process which yields a highly cross-linked gelatin matrix with high mechanical and thermal stability. When used in cell cultures, cells can attach to both the external and the internal surfaces of the matrix. The increased surface area of the matrix together with the protection from stress afforded to the cells in the interior of the matrix results in enhanced cell production capabilities. An additional advantage of the product is that the matrix can be dissolved with proteolytic enzymes resulting in the harvesting of cells with almost 100% viability.

In one embodiment, the microcarrier is a CULTISPHER-G microcarrier. CULTISPHER-G has a particle diameter of 130-380 μm, a volume of 12-18 ml/g dry, a density of 1.04 g/ml with an average pore diameter of 20 μm.

In order to prepare and use CULTISPHER-G microcarriers, reference can be made to inter alia Biotech. Bioeng. (2000) 68, 1 p 59-70; Brit. J. Cancer. Suppl. XXVII, S-78-S82 (1996); and the manufacturer's website.

CYTOPORE 2 Microcarrier

CYTOPORE microcarriers are available from GE Healthcare (previously Amersham). Cytopore is made of 100% cellulose, which is not-toxic to the cells and biodegradable. It is positively charged, due to the N,N,-diethylaminoethyl groups. It has a very precise particle size distribution and a network structure, the ratio of surface area to particle material is more than 95 to 1. The network structure enables stained cells to be closely observed while they grow inside the microcarriers. The typical particle diameter is 200-280 μm and effective surface area is 1.1 m2/g dry. The relative density is 1.03 g/ml, the average diameter of pore openings is 30 μm and the volume is 40 ml/g dry. In order to prepare and use CYTOPORE microcarriers reference is made to inter alia *Applied Microbiology and Biotechnology* (1997) 47, 4 p 352-7; *Cytotechnology* (1999) 30 p 143-147; *Chinese Journal of Biotechnology* (1999) 15, 4 p 239-44 and *Acta Oto-Laryngologica* (2002) 122, 5 p 541-5.

CYTOPORE 2 has been optimised for anchorage-dependent cells requiring a charge density around 1.8 meq/g.

In some embodiments, the microcarrier is a porcine gelatin microcarrier.

In some embodiments, the microcarrier is made of 100% cellulose.

Advantageously, microcarriers with a strong positive charge are optimal with tags carrying a strong negative charge.

Tags

As described above, tags may be used as labels or tags which are conjugated to a microcarrier—such as a cell-associated microcarrier. Subsequent detection and identification provides for an unambiguous record of the chronology and identity of the cell culture conditions to which the cell unit has been exposed.

Various molecular or macromolecular tags may be used in combination with the microcarriers so long as they can be detected. The tags typically comprise uniquely shaped or objects modified with markings and/or coloured and/or fluorescent compounds.

In one embodiment the tags which are used to label cell units have one or more (preferably all) of the following qualities:
  i. They are small in size relative to the microcarrier they are labelling and/or smaller than the mean pore size of a porous microcarrier;
  ii. They are capable of forming a complex with the microcarrier such that binding persists throughout the experiment and so unbound tags can be separated from the complex without affecting the labelled cell units;
  iii. They are separable from cell units with which they have formed a complex under conditions which do not perturb the unique qualities of the tags
  iv. They are made of one or more inert substances which do not substantially affect the biology of the cell unit and which in turn is not affected by the cell units or their biology;
  v. They are obtainable in large numbers and moreover in many related but distinct variants which are easily distinguishable using an appropriate technique;
  vi. They are distinguished by a method which is convenient, highly reliable and which can be automated.

In one embodiment, the tag is a microsphere—such as a fluorescent and/or coloured microsphere.

More than 2000 different microspheres made by emulsion or suspension polymerization, precipitation etc. and comprised of polystyrene, other polymers, copolymers, terpolymers and/or silica etc. are available in a variety of sizes, densities, colours etc, for example from Duke Scientific Corporation (Palo Alto Calif., USA) or Bangs Laboratories Inc. (Fishers Ind., USA).

A common type of microsphere is the Polystyrene (PS) and styrene/divinylbenzene copolymer (S/DVB) microsphere. Other polymers include polymethylmethacrylate (PMMA), polyvinyltoluene (PVT), styrene/butadiene (S/B) copolymer, styrene/vinyltoluene (S/VT) copolymer. Many of these microspheres can be functionalised, for instance by carboxyl groups as in the CML microspheres, or by amino functionalized or nitrogen-containing compounds, like primary, secondary, tertiary, and quaternary aliphatic amines, aromatic amines, and pyridines, which offer alternative coupling reactions to the COOH beads.

Suitably, the microsphere is a hydrophilic microsphere. More suitably the microsphere is a polystyrene microsphere. Most suitably, the microsphere is a surface-modified microsphere such as a carboxylate modified (CML) microsphere from Duke Scientific Corporation (Palo Alto Calif., USA).

In one embodiment, one or more CML microspheres are complexed together with one or more CYTOPORE 2 microcarriers.

CML microspheres have a highly charged surface layer of carboxyl groups derived from a copolymerisation process. The surface is somewhat porous and relatively hydrophilic, but retains overall hydrophobic properties. The charge density of these particles ranges from about 10-125 $Å^2$ per carboxyl group, and they are stable to high concentrations of electrolytes (up to 1M univalent salt). The CML latex will adsorb proteins and other biomolecules, but much less strongly than hydrophobic microspheres.

In some embodiments, conjugates of microspheres and proteins, e.g. streptavidin are prepared.

For example, conjugates with CML microspheres may be prepared as follows. CML microspheres may be activated using a water soluble carbodiimide reagent that makes the carboxyl groups reactive with primary amines on the proteins to be coupled. A 50 mM reaction buffer at pH 6.0 is prepared. Sodium acetate or 2-[N-morpholino)ethanesulfonic acid (MES) are suitable buffers. The protein is dissolved in the reaction buffer at a concentration of 10 mg/mL. A 1% (w/v) suspension of microspheres is prepared in the reaction buffer. One volume protein solution to ten volumes microsphere suspension is prepared and the mixture allowed to incubate, at room temperature for 20 minutes. A solution of 10 mg/mL (52 µMol/mL) of 1-ethyl-3-(3-dimethylaminopropyl)carbodiimide (EDAC) in deionized water is prepared and used immediately. A calculated amount of EDAC solution to the microsphere suspension is added and the pH of the reaction mixture adjusted to 6.5±0.2 with 0.1N NaOH. The mixture is incubated on a rocker or mixing wheel for 2 hours at room temperature. Unbound protein is removed and stored in storage buffer.

Advantageously, CML and other microspheres can be obtained in various formats—such as various colors (e.g. blue, red, green, yellow, black), various fluorophores (e.g. Fluorescein (green), Fluorescein (red) or Fluorescein and Rhodamine (red green) and various sizes (e.g. 5.4 µm (1.14× $10^{10}$ beads/gram), and 7.6 µm (4.10× $10^9$ beads/gram)).

CML and other microspheres may be prepared such that they are loaded with one or more visible dyes and/or fluorophores.

In one embodiment, tags—such as microspheres—are not coated with proteins.

Advantageously, CML microspheres not coated with proteins (e.g. streptavidin) are highly negatively charged and they adhere extremely tightly to CYTOPORE microcarriers, which carry a high positive charge. The ratio of CML microsphere(s): CYTOPORE microcarrier(s) required to give bulk complexes may be as low as about 1:1. In previous systems that the present inventors have used a ratio of about 1:250 was required in order to obtain even a few bound tags in each complex after multiple washes.

By varying various parameters in the fabrication process, commercial microsphere providers—such as Bangs Laboratories—can manufacture bead sets which can be distinguished based on differing sizes (e.g. bead sets of 4.4 µm and 5.5 µm diameter). Beads within each size group can be furthermore distinguished from each other based on differing fluorescence intensity owing to differential loading with a single fluorescent dye. It is possible to use many different dyes with different absorption or emission characteristics, Which can be attached to the microcarriers described herein. Accordingly, Tag diversity may result from varying tag size and/or fluorophore loading (i.e. fluor intensity) and/or fluorophore identity/combination. In particular, Tag diversity may result from the type of fluorophore they carry (e.g. beads can be loaded with either UV2 or Starfire Red); size (e.g. for each fluorophore there are 5 different bead sizes: 1.87, 4.41, 5.78, 5.37 and 9.77 microns) and/or the quantity of fluorophore they carry (5 different intensities of each dye are available). Other fluorophores—such as TRITC may be used.

Filters can then be used to detect the at least 4 different dyes on any given bead—such as the TRITC filter (ex 540/25; dm 565; ba 605/55) for TRITC visualization from Nikon; the DAPI filter (ex 340-380; dm 400; ba 435-485) for UV2 visualization from Nikon; the GFP-B filter (ex 460-500; dm 505; ba 510-560) for FITC visualization from Nikon and the Cy5 filter set (cat no 41008 from Chroma Technology) for Starfire Red visualization.

Microspheres can be dyed internally or externally, with visible or fluorescent dyes. Internal dyeing occurs when the dye is integrated into the microsphere mass, typically by soaking the microsphere in a solution containing a dye or fluorophore. External modification occurs when a dye is conjugated to the surface of the microsphere, for instance modification of a CML microsphere with an isothiocyanate derivative as described herein.

Accordingly, in some embodiments, the microsphere may be dyed internally or externally, with visible or fluorescent dyes.

It is furthermore possible to use 'quantum dots' to obtain a very high number of different fluorescent labels which can be read conveniently. Thus, in a further embodiment of the present invention, Quantum dots instead of fluorophores are used. In certain embodiments, quantum dots are preferable due to the fact they do not fade (photo-bleach) when exposed to light. For instance the fluorophore FITC is known to photo-bleach and cell units treated with tags containing FITC are ideally handled in the dark and are difficult to analyse reliably. Quantum dots may be incorporated into microspheres at the time of polymerizing the polystyrene resulting in even loading of tags. Quantum dots are available in many colours and they can be excited at the same wavelength so allowing visualization of multiple colours without filters, by using a colour CCD camera. Further background information on Quantum dots is available from U.S. Pat. No. 6,322,901, U.S. Pat. No. 6,576,291, US2003/0017264, U.S. Pat. No. 6,423,551, U.S. Pat. No. 6,251,303, U.S. Pat. No. 6,319,426 U.S. Pat. No. 6,426,513, U.S. Pat. No. 6,444,143, US2002/0045045, U.S. Pat. No. 5,990,479, U.S. Pat. No. 6,207,392, U.S. Pat. No. 6,251,303, U.S. Pat. No. 6,319,426, U.S. Pat. No. 6,426,513 and U.S. Pat. No. 6,444,143.

Advantageously, the tags are protected against degradation by the components of the cell culture, for example by chemical or other modification or by encapsulation. Encapsulation of tags can take place in many different media, for example in beads as already described herein—such as those from Bangs Laboratories Inc. (Fishers Ind., USA), and encapsulation may be used to standardise tag dosage in addition to providing components for tag amplification and/or detection (for example by providing PCR primers for use with a DNA tag).

Detection of tags can be accomplished by a variety of methods familiar to those skilled in the art. Methods include mass spectrometry, nuclear magnetic resonance, sequencing, hybridisation, antigen detection, electrophoresis, spectroscopy, microscopy, image analysis, fluorescence detection, etc. In some embodiments, since the tags typically contain a colour or a fluorophore then microscopy, spectroscopy, image analysis and/or fluorescence detection are used.

The tags do not necessarily have to be distinguished by their chemical or molecular structure in the first instance. Multiple variations of the non-chemical tagging strategy can be devised to determine the identity of a given cell unit in a mixture or of deducing the identity of the different cell units that comprise a mixture. For instance optical or visual methods of tagging have been described where different shaped objects, graphically encoded objects or different colours denote the identity of a sample (for example see 1998, Guiles et al, Angew. Chem. Intl Ed Engl, vol. 37, p 926; Luminex Corp, Austin Tex., USA; BD Biosciences; Memobead Technologies, Ghent, Belgium).

Suitably, the tag may be a charged tag (e.g. a negatively charged tag). Accordingly, in a further aspect, there is provided a complex comprising a microcarrier—such as a porous microcarrier—and a charged tag.

Typically, the microcarrier has a net charge. It may comprise, consist or consist essentially of protein, cellulose, polyethylene, polystyrol, glass collagen, collagen glucose-aminoglycan and/or gelatin. Accordingly, the microcarrier may be selected from the group consisting of a CYTOPORE microcarrier, a CYTOPORE 1 microcarrier, a CYTOPORE 2 microcarrier, a CULTISPHER microcarrier, a CULTISPHER-G microcarrier, a CULTISPHER-GL microcarrier and a CULTISPHER-S microcarrier, an INFORMATRIX microcarrier, a MICROSPHERE microcarrier, a SIRAN microcarrier, and a MICROPOROUS MC microcarrier.

Suitably, the charged tag is a sphere—such as a microsphere that is about 9 µM or less in diameter. The microsphere may be a carboxylate modified (CML) microsphere.

In a further embodiment, the tag is a rod-shaped particle. Suitably, the rod-shaped tag is a nanowire. The nanowire may comprise, consist or consist essentially of various metals—such as aluminium. The nanowire may be coated with various metals—such as silver and/or gold. Suitably, the nanowire is about 1 µM or less in diameter and/or is about 10 µM or less in length.

The nanowire may be a nanowire as described in Science vol. 294, p. 137-141 (2001). Accordingly, in a further aspect, there is provided a complex comprising a microcarrier and a nanowire. Briefly, nanowires are multimetal microrods intrinsically encoded with submicrometer stripes. Complex patterns can be generated by sequential electrochemical deposition of metal ions onto templates with uniformly sized pores. Advantageously, the nanowires are small enough to be used as tags that may be added after each split. This is more convenient as it is necessary to read tags only in the positive microcarriers.

Parameters for the rod-shaped particle—such as the nanowire—include but are not limited to size, optical properties and/or metal composition. In one embodiment, the optical properties are selected from the group consisting of: light reflectivity—such as light reflectivity of a particular wavelength, colour, the fluorescence emission wavelength(s) and the fluorescence emission intensity.

In some embodiments, the rod-shaped particle—such as the nanowire is externally dyed.

The microcarrier that is used together with the rod-shaped tag may be a porous microcarrier—such as a charge neutral microcarrier.

The microcarrier may comprise, consist or consist essentially of protein, cellulose, polyethylene, polystyrol, glass, collagen, collagen-gylcose-aminoglycan and/or gelatin. The microcarrier may be selected from the group consisting of a CYTOPORE microcarrier, a CYTOPORE 1 microcarrier, a CYTOPORE 2 microcarrier, a CULTISPHER microcarrier, a CULTISPHER-G microcarrier, a CULTISPHER-GL microcarrier and a CULTISPHER-S microcarrier, an INFORMATRIX microcarrier, a MICROSPHERE microcarrier, a SIRAN microcarrier, and a MICROPOROUS MC microcarrier.

In one embodiment, the microcarrier that is used together with the rod-shaped microcarrier is a CULTISPHER microcarrier—such as a CULTISPHER-G microcarrier, a CULTISPHER-GL microcarrier or a CULTISPHER-S microcarrier. In one embodiment, the microcarrier that is used together with the rod-shaped microcarrier is a CULTISPHER-G microcarrier.

Advantageously, it has been found that using rod shaped tags and charge-neutral porous microcarriers is better than using spherical tags on the same microcarriers. Without wishing to be bound by an particular theory it is believed that smaller tags penetrate the pores of the microcarriers better and become jammed (presumably due to size asymmetry). Accordingly, the binding of nanowires is better than, for example, the binding of microsphere tags and results in a high level permanent tagging.

In another embodiment, one or more polystyrene microbeads are complexed together with one or more CULTISPHER-G microcarriers.

For some embodiments, the tag is not a DNA tag.

In some embodiments, the tag is an externally dyed tag.

Stem Cells

Stem cells are described in detail in Stem Cells: Scientific Progress and Future Research Directions. Department of Health and Human Services. June 2001. The contents of the report are herein incorporated by reference.

There is still considerable debate about what constitutes a stem cell, however for the purposes of this discussion a key characteristic is the ability to differentiate into a different cell type. Examples of stem cells are given below.

Various factors that have been used to induce directed differentiation of stem cells include: retinoic acid, epidermal growth factor (EGF), bone morphogenic proteins (BMPs), basic fibroblast growth factor (bFGF), activin-A, transforming growth factor beta-1 (TFG β-1), hepatocyte growth factor, nerve growth factor, sonic hedgehog (SHH), interleukin-3 (IL-3), interleukin-6 (IL-6), granulocyte macrophage colony stimulating factor (GM-CSF), erythropoietin, vitamin D3, dexamethasone, β-mercaptoethanol, butylated hydroxyanisole, 5-azacytidine, DMSO, insulin, thyroid hormone (T3), LIF, foetal calf serum, vascular endothelial growth factor (VEGF), steel factor, variations in oxygen concentration, ascorbic acid, β-glycerophosphate, nicotinamide, platelet derived growth factor (PDGF), cAMP, various cell adhesion molecules and substrates, and others. In addition to these defined factors, it is likely that undefined extracts, such as conditioned media, human and animal tissue homogenates, or plant extracts can be used to direct stem cell differentiation. Progressive fractionation of these undefined extracts may yield active fractions or even pure components with high potency. These factors can be added to the growth medium used in a particular experiment, either alone, or in combination, or in a defined order which is crucial to the experimental result.

Formation of Cell Units

Groups of cells (cell colonies) can be grown in cell culture under various conditions and the colony can largely maintain its integrity under various conditions, when disturbed, and when mixed with other colonies. Such groups or colonies are referred to herein as cell units. Formation of cell units may be achieved, by way of illustration, by growing cells as adherent cultures on solid substrates such as carriers. If cell proliferation occurs after seeding on the carriers, the daughter cells will attach on the same carrier and form part of the same colony. In general, live adherent cells do not readily dissociate from their growth substrate, and so the integrity of the cell colony persists despite any mechanical manipulation of the carrier, agitation of the culture medium, or transfer into another tissue culture system. Similarly, if at any time multiple carriers are placed in the same vessel (e.g. beads are pooled) then there will be no substantial transfer of cells from one bead to another.

An important advantage of forming cell units on solid substrates is that the substrate—and therefore the attached cells by reason of association—can be labelled as described herein.

When cells are grown on smaller carriers they can be treated as a suspension culture. A common method of growing cells on small carriers is referred to as microcarrier cell culture (see 'Microcarrier cell culture, Principles and Methods', Edition AA, available from Amersham Biosciences (18-1140-62); herein incorporated in its entirety by reference).

Microcarrier cultures are used commercially for antibody and interferon production in fermenters of up to 4000 litres.

As the physical properties of carriers are well known it is easy to calculate the number of carriers used in an experiment. The carriers may be available as dried products, which can be accurately weighed, and subsequently prepared by swelling in liquid medium. In addition the number of cells used to inoculate a microcarrier culture can be worked out and varied.

Harvesting of cells grown on the microcarriers described herein, or liberation of labels from microcarriers, can be achieved by enzymatic detachment of cells, and/or by digestion of the carrier where applicable as described herein.

Separation of Tags from Labelled Cell Units

In a further aspect, the present invention provides improved methods for the separation of tags from cell units (e.g. cell units complexed with microcarriers).

Advantageously, when the tags are separated in accordance with the methods described herein, they are obtained in an intact state such that the unique parameters of each tag can be measured faithfully.

Advantageously, when the tags are separated in order to be analysed by an optical method—such as by microscopy—they are furthermore obtained in close proximity to each other such that the they can be imaged conveniently (e.g. using just one or two image fields).

In one aspect, there is provided a method for separating a complex comprising a microcarrier and a tag, comprising the step of contacting said complex with a protease, wherein said microcarrier comprises, consists or consists essentially of protein.

Suitably, the microcarrier comprises, consists or consists essentially of collagen and/or gelatin—such as a CULTISPHER microcarrier (e.g. a CULTISPHER-G microcarrier, a CULTISPHER-GL microcarrier and CULTISPHER-S microcarrier).

The protease may be proteinase K, typsin, thermolysin and/or caspase.

If the protease is proteinase K then in some embodiments, it is used in an amount of about 0.5 U/ml or more. Suitably, the complex is contacted with proteinase K for at least about 20-60 minutes. Suitably, the complex is contacted with the protease in a volume of about 5 µl or less.

In a further aspect, there is provided a method for separating a complex comprising a microcarrier—such as a porous microcarrier—and a tag, comprising the step of contacting said complex with acid.

Suitably, the microcarrier has a net charge and may comprise, consist or consist essentially of cellulose. Thus, by way of example, the microcarrier may be a CYTOPORE microcarrier—such as is a CYTOPORE 2 microcarrier.

In some embodiments, the tag is a sphere—such as a microsphere—that comprises, consists or consists essentially of polystyrene.

In some embodiments, the tag is a rod-shaped particle—such as a nanowire.

Various reagents may be used for the liberation of tags from microcarrier—such as acid (e.g. Hydrocholoric acid and/or sulphuric acid) or sodium hypochlorite and/or sodium hydroxide in addition to other reagents—such as trypsin-EDTA, cellulase, proteinase K, and sodium chloride (e.g. 5M sodium chloride).

In some embodiments, the reagent is hydrochloric acid, preferably 37% hydrochloric acid (about 12 M).

In some embodiments, the reagent is sodium hypochlorite.

In some embodiments, the reagent is a protease.

In some embodiments, the reagent is a proteinase K.

Suitably, the digestion of the one or more microcarriers is carried out on an optically clear surface—such as a glass microscope slide. This allows convenient imaging in situ which is advantageous as no material is lost.

Suitably, the surface is treated to prevent the spreading of a liquid containing the microcarrier, for instance using a siliconising (silanising) agent.

Suitably, the microcarriers to be digested are washed in distilled water to remove any traces of medium and/or salts and applied to the surface in a minimal volume of liquid Suitably, the surface is heated to achieve complete dehydration of the microcarriers and to adhere the tags to the surface, thus preventing dispersal.

In order to carry out microcarrier digestion in a minimal volume, preferably less than 5 µl and more preferably less than 2 µl, the digestion is performed in a humidified box.

In some embodiments, the digestion is achieved using one or more proteases. The protease solution is typically dispended directly onto the dried microcarriers and placed in the humidified box. Once the microcarriers have dissolved (typically 30-60 mins) the slides are removed from the humidified box to check for complete digestion. The protease solution is evaporated and complete drying of the released tags onto the slide is provided for to allow the tags to be analysed.

In some embodiments, the digestion of the one or more microcarriers is carried out in a microcentrifuge or PCR tube such as those manufactured by Eppendorf. The interior of the tubes may be treated to prevent the tags from adhering to it once they are liberated from the microcarriers.

In some embodiments, the tubes are placed in a PCR machine allowing for precise temperature control.

In some embodiments, the PCR machine operates a heated lid, allowing for use of minimal volumes of liquid.

Suitably, once the one or more tags have been separated from the cell unit(s) and the tag(s), one or more images of the tag(s) may be obtained (using, for example, a microscopic technique). The images may then be analysed to determine one or more features of the tag.

In a further aspect, there is also provided a method for identifying one or more tags that are obtained or obtainable from one or more cell units comprising the steps of: (a) separating the cell unit(s) and the tag(s); (b) obtaining one or more images of the tag(s) (e.g. by using a microscopic technique); and (c) analysing the images to determine one or more features of the tag. Suitably, the one or more features of the tag may be used to determine the cell culture history of the cell unit(s) from which the tag(s) was derived or obtained.

Combinatorial Serial Culture of Cells
Split-Pool Cell Culture

Forming cell units (particularly microscopic cell units) is furthermore useful for sampling multiple tissue culture conditions as each cell unit constitutes an easily handled unit that can be exposed to a variety of cell culture conditions. In accordance with the present invention, cell groupings are typically produced by growing cells in microcarrier culture, and the terms cell unit, cell group, colony and bead are used interchangeably. A particularly efficient method for sampling a large number of cell culture conditions is referred to as Combinatorial Cell Culture or split-pool cell culture and in one embodiment involves the serial subdividing and combining of groups of cell units in order to sample multiple combinations of cell culture conditions. In one aspect of the invention the method operates by taking an initial starter culture (or different starter cultures) of cell units divided into $X_1$ number of aliquots each containing multiple beads (groups/colonies/carriers) which are grown separately under different culture conditions. Following cell culture for a given time, the cell units can be pooled by combining and mixing the beads from the different aliquots. This pool can be split again into $X_2$ number of aliquots, each of which is cultured under different conditions for a period of time, and subsequently also pooled. This iterative procedure of splitting, culturing and pooling (or pooling, splitting and culturing; depending on where one enters the cycle) cell units allows systematic sampling of many different combinations of cell culture conditions. The complexity of the experiment, or in other words the number of different combinations of cell culture conditions tested, is equal to the product of the number of different conditions ($X_1 \times X_2 \times \ldots X_n$) sampled at each round. Note that the step of pooling all the cell units prior to a subsequent split can be optional—a step in which a limited number of cell units are pooled can have the same effect. The invention therefore embodies a number of related methods of systematically sampling multiple combinations of cell culture conditions where groups of cell units are handled in bulk.

Regardless of the precise manner in which a diversity of cell culture conditions is sampled by this means the procedure is efficient because multiple cell units can share a single vessel, where they are cultured under identical conditions, and it can be carried out using only a few culture vessels at any one time (the number of culture vessels in use is equal to the number of split samples). In many respects the principle of this procedure resembles that of split synthesis of large chemical libraries (known as combinatorial chemistry), which samples all possible combinations of linkage between chemical building block groups (see for example: Combinatorial Chemistry, Oxford University Press (2000), Hicham Fenniri (Editor)). Split-pool cell culture can be repeated over any number of rounds, and any number of conditions can be sampled at each round. So long as the number of cell units (or colonised beads in this example) is greater than or equal to the number of different conditions sampled over all rounds, and assuming that the splitting of cell units occurs totally randomly, it is expected that there will be at least one cell unit that has been cultured according to each of the various combinations of culture conditions sampled by the experiment. This procedure can be used to sample growth or differentiation conditions for any cell type, or the efficiency of biomolecule production (e.g. production of erythropoietin or interferon) by any cell type. Because the procedure is iterative, it is ideally suited to testing multistep tissue culture protocols—for instance those described above in connection with stem cell differentiation. The variables which can be sampled using this technique include cell type, cell grouping (e.g. microcarrier culture, cell encapsulation, whole organism), growth substrate (e.g. fibronectin on microcarrier), duration of cell culture round, temperature, different culture media (including different concentrations of constituents), growth factors, conditioned media, co-culture with various cell types (e.g. feeder cells), animal or plant extracts, drugs, other synthetic chemicals, infection with viruses (incl. transgenic viruses), addition of transgenes, addition of antisense or anti-gene molecules (e.g. RNAi, triple helix), sensory inputs (in the case of organisms), electrical, light, or red-ox stimuli and others.

Split-Split Cell Culture

The purpose of performing split-pool processes on cell units is to systematically expose these to a pre-defined combination of conditions. The person skilled in the art will conceive of many different means of achieving this outcome. In addition to split-pool processes and variations thereof, it is worthwhile briefly discussing split-split processes. A split-split process involves subdividing a group of cell units at least twice, without intervening pooling of cell units. If split-split processes are used over a large number of rounds, the number of separate samples that are generated increases exponentially. In this case it is important to employ some level of automation, for example the use of a robotic platform and sophisticated sample tracking systems. The advantage of split-split steps is that (since cell units are not combined) it is possible to segregate lineages of the various cell units based on their cell culture history. Consequently split-split steps can be used to deduce if a particular cell culture condition is responsible for any given cellular process and therefore used to deduce the culture history of cell units.

Predetermined Protocols

The splitting and/or pooling of cell units may be accomplished totally randomly or may follow a predetermined protocol. Where cell units are split and/or pooled randomly, the segregation of a given cell unit into any group is not predetermined or prejudiced in any way. In order to result in a high probability that at least one cell unit has been exposed to each of the possible combinations of cell culture conditions, it is advantageous to employ a larger number of cell units than the total number of combinations of cell culture conditions that are being tested. Under certain circumstances it is therefore advantageous to split and/or pool cell units according to a predetermined protocol, the overall effect being that adventitious duplications or omissions of combinations are prevented. Predetermined handling of cell units can be optionally planned in advance and logged on a spreadsheet or computer programme, and splitting and/or pooling operations executed using automated protocols, for instance robotics. Labelling of cell units (see below) can be by any of a number of means, for instance labelling by RFID, optical tagging or spatial encoding. Robotic devices capable of determining the identity of a sample, and therefore partitioning the samples according to a predetermined protocol, have been described (see 'Combinatorial Chemistry, A practical Approach', Oxford University Press (2000), Ed H. Fenniri). Alternatively, standard laboratory liquid handling and/or tissue culture robotics (for example such as manufactured by: Beckman Coulter Inc, Fullerton, Calif.; The Automation Partnership, Royston, UK) is capable of spatially encoding the identity of multiple samples and of adding, removing or translocating these according to pre-programmed protocols.

Analysis and/or Separation of Cell Units

Following each round of cell culture, or after a defined number of rounds, the cell units can be studied to observe any given cellular process that may have been affected by the tissue culture conditions.

The invention will now be further described by way of Examples, which are meant to serve to assist one of ordinary skill in the art in carrying out the invention and are not intended in any way to limit the scope of the invention.

EXAMPLES

Example 1

Biotin-Conjugation of CULTISPHER-G Microcarriers

Fluorescent microspheres (tags) from Bangs labs are streptavidin-coated and so the CULTISPHER-G microcarriers (CSG) are biotinylated in order to facilitate binding of the two during the course of a split-pool experiment. CSG are supplied dry and are hydrated in excess sterile PBS overnight (according to manufacturer's instructions) and autoclaved. They are then rinsed several times in sterile PBS.

Example 2

Biotinylation Reagent

The biotinylation reagent, Biotinamidohexanoyl-6-aminohexanoic acid N-hydroxysuccinimide ester (Sigma B3295 10 mg) is used. 10 mg of the reagent is dissolved in 400 µl dimethylformamide (DMF) and added to 5 ml settled volume of hydrated CSG (5 ml settled volume in 50 ml tube) and mixed well by gentle pipetting (0.1% v/v BSA/PBS is pipetted up/down into the pipette tips beforehand to prevent sticking of CSG to the inside surface of the tips).

The biotinylation reagent is allowed to incubate with the CSG overnight at room temperature before several rinses in sterile PBS to remove excess biotinylation reagent (rinsing is performed in a 50 ml tube with the CSG being allowed to settle between rinses and careful aspiration with a vacuum).

The biotinylated CSG are now ready for use in an experiment. They are stored under sterile conditions in a known volume of PBS and the concentration in mixed suspension is calculated based on this volume and the dry mass of CSG added to the tube initially (typically we have 2000 CSG in 100 µl)

Example 3

Tagging Methods in Wells and Columns

After the seeding of CSG with ES cells, the fluorescent tags are added to tag each stage in the split-pool matrix. The following method for tagging biotinylated CSG with streptavidin-coated tags is used.

The experiments are conducted in a 5×5 well (10 cm×10 cm) cell culture dish (each well therefore measures 2 cm×2 cm). Typically, one well will contain 7000 CSG/ES cell complexes.

The fluorescent tags are added to the well at a known concentration of tags/CSG. The mixture is gently pipetted to mix (using 0.1% BSA/PBS-treated tips to prevent sticking) and then the whole 5×5 dish is tilted to facilitate close contact of the CSG and tags.

The dish is placed in a 37° C. incubator for approximately 1 hr and then placed flat until the next stage of the split-pool experiment.

Example 4

Washing Methods and Sieving

Figure 2:
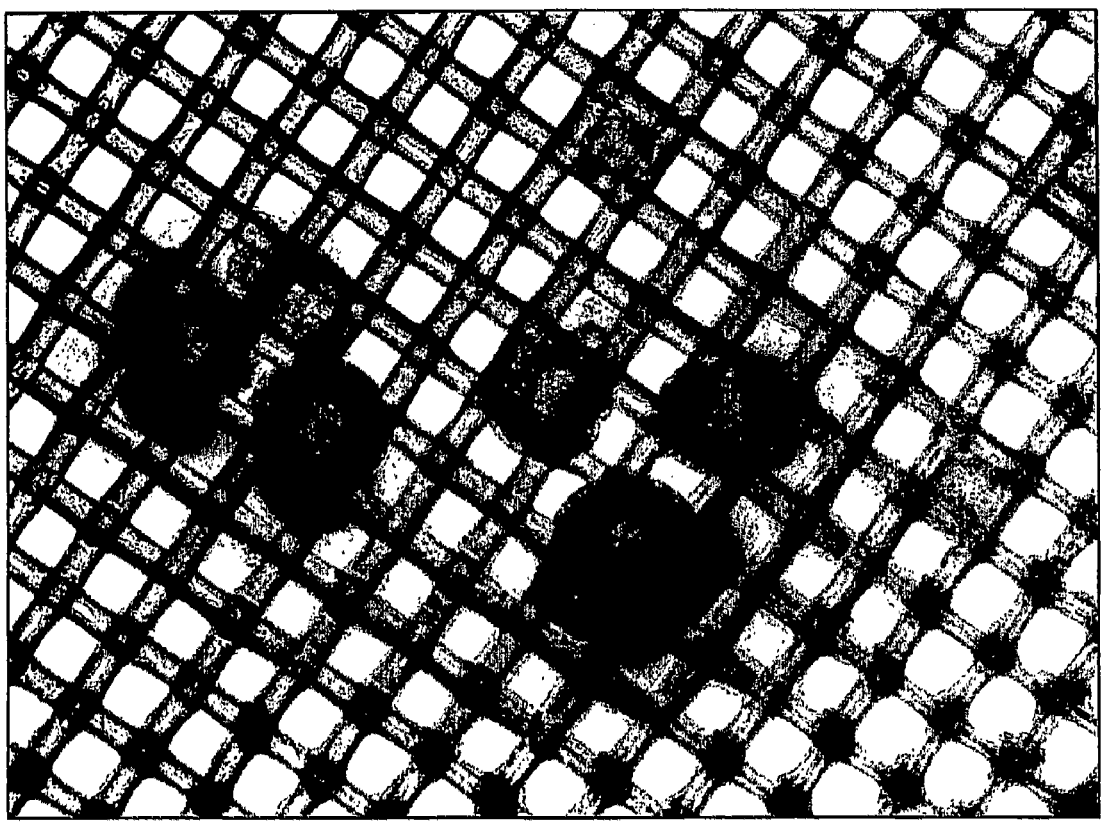

The contents of the wells which have received the same treatment are gently pooled together and washed through a 70 µm sieve. The CSG are larger than 70 µm and are caught in the sieve (see FIG. 2). A minimal volume of PBS (typically 5 ml) is washed through the sieve to remove unbound, fluorescent tags and the sieve is then inverted and <3 ml basal medium washed through to collect the GSG/tag complexes.

The contents of all wells containing different culture conditions are washed separately before being pooled together prior to splitting for the next round of culture conditions.

Example 5

Digestion of CSG and CYTOPORE 2

Figure 1:
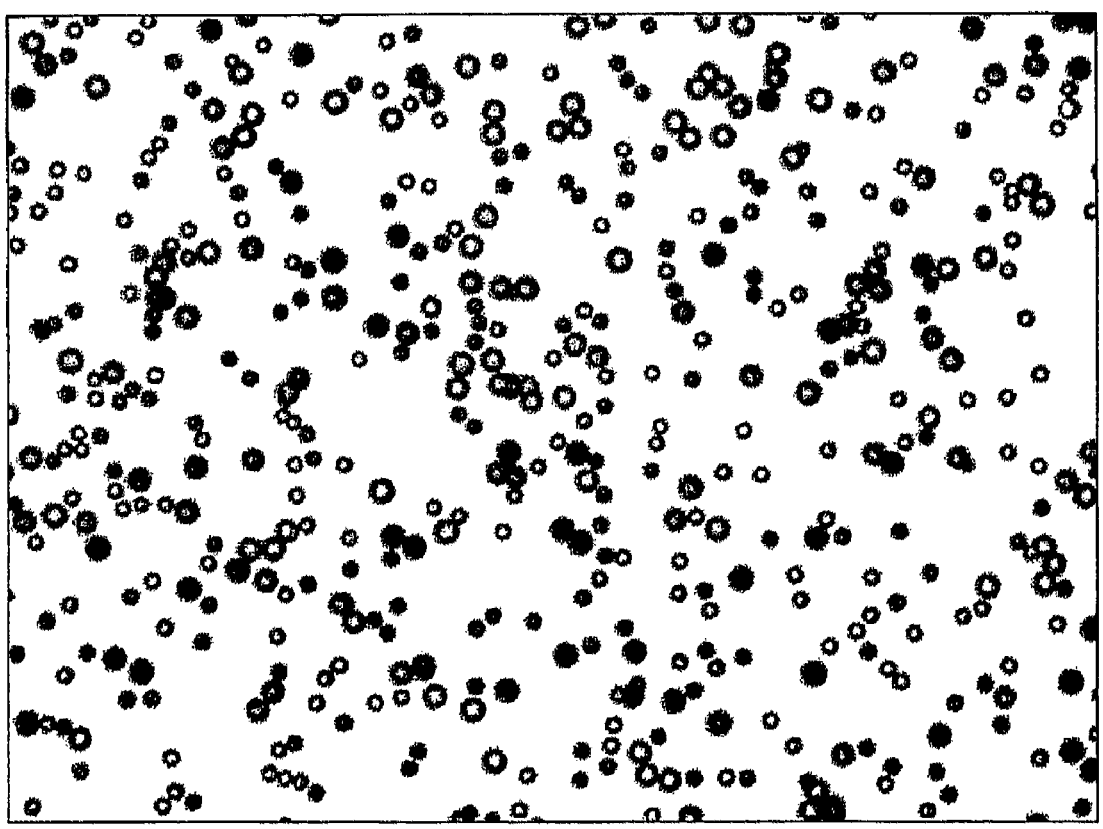
FIG. 1 shows a sample of coloured Duke microbeads viewed under light microscopy with Black, Red and Blue tags in two different sizes (5.4 μm and 7.6 μm).

The following methods are used to digest the beads prior to analysis of the attached fluorescent Bangs' tags or non-fluorescent Duke tags (as shown in FIG. 1) on CYTOPORE 2 or CSG.

(a) CSG

Figure 3:
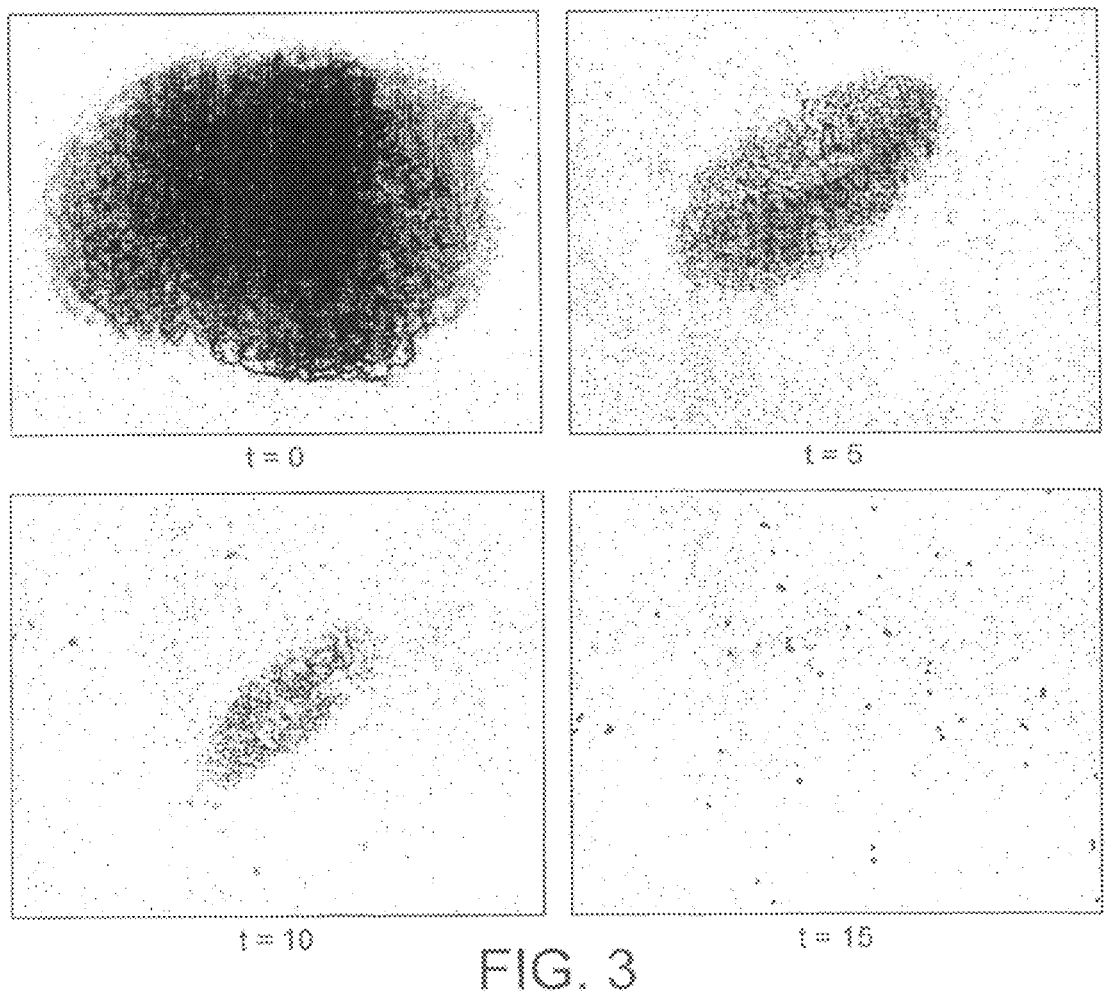
FIG. 3 shows the digestion of CULTISPHER-G microcarriers with 2 U/ml proteinase k (figures show the same microcarrier over a 15 minute period, as indicated).

Incubation of individual CSG beads in 2 U/ml proteinase K (Sigma P4850) in wells of glass-bottomed, 384-well microtitre plates results in complete digestion of the CSG bead whilst leaving the polystyrene, fluorescent tags intact. Complete digestion is typically complete within 20 mins and the fluorescent tags then remain in the proteinase k solution indefinitely, without inactivation of proteinase k, with no detrimental effect to the tags or their fluorescence (see FIG. 3).

(b) CYTOPORE 2

Figure 4:
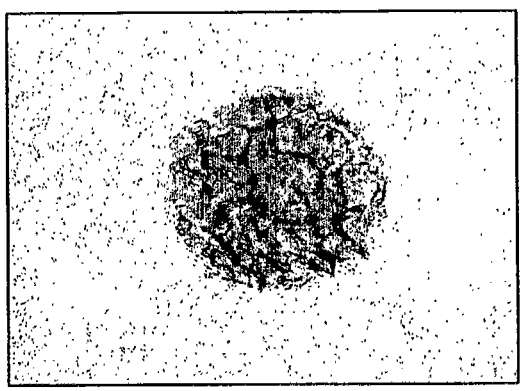
FIG. 4 shows the digestion of CYTOPORE 2 microcarriers with 37% HCl (~12M) (figures show the same microcarrier over a 1 hr 30 m period, as indicated).
Figure 4:
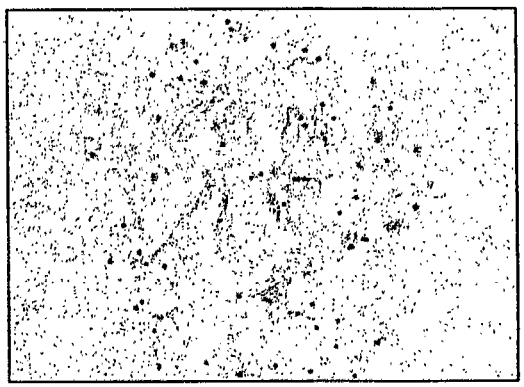
Figure 4:
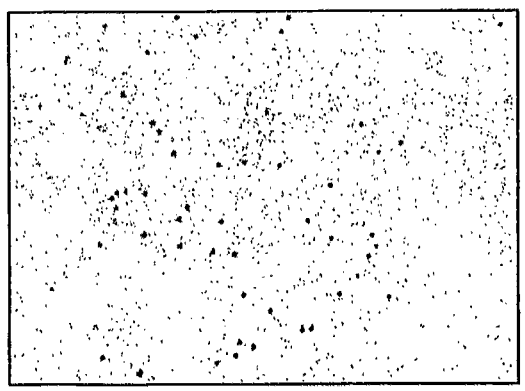

Incubation of CYTOPORE 2 microcarriers (made from cellulose) in 37% HCl (.about.12M) results in complete digestion of the microcarrier within 90 minutes whilst leaving the attached coloured Duke tags intact. As with the CSG, the tags remain in the digestion medium indefinitely, without inactivation and with no detrimental effect to the tags (see FIG. 4).

Example 6

Flowchart

Figure 5:
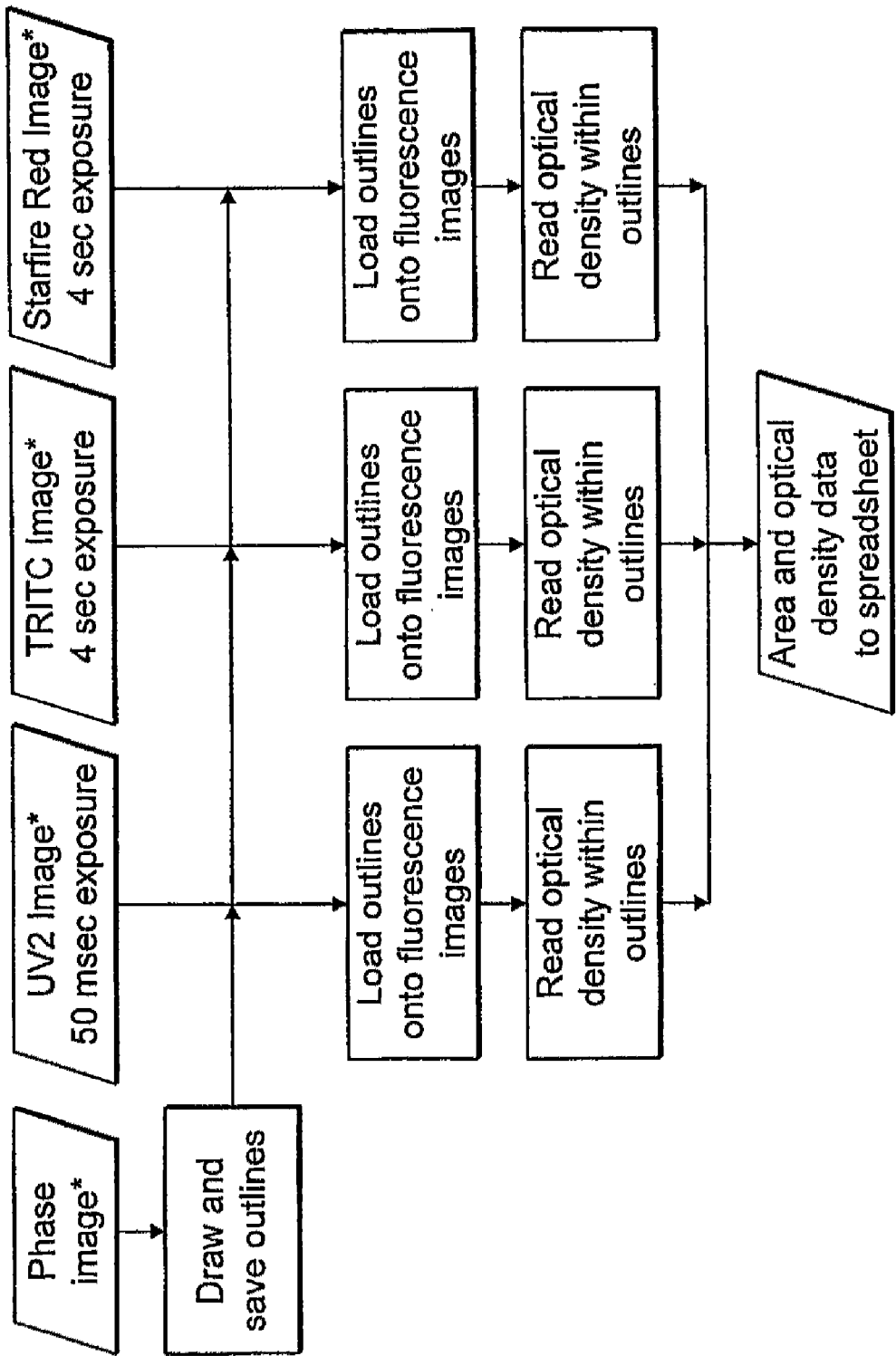
FIG. 5 shows an Imagepro Tag Analysis Flowchart for microscope analysis to identify one or more area and/or optical density values for a microbead. Images are taken using various exposures and filters: UV2 filter: Ex 340-380 nm; Em 435-485 nm; TRITC filter: Ex 540/25 nm; Em 605/55 nm; Starfire Red: Ex 620/60 nm; Em 700/75 nm.

A spreadsheet is prepared which examines tags in parallel for UV2 (and rhodamine) and Starfire Red (and fluorescein) fluorescence, i.e. the flowchart shown in FIG. 5 is duplicated in parallel with all references to Fluorescence 1 replaced with Fluorescence 4, and Fluorescence 3 with Fluorescence 2. For this system the final 'No' decisions from pages 2 and 4 will go to a "No Call".

This system can result in a tag remaining unidentified, or given two identities. The latter can occur if the thresholds for the lowest intensity tags are set incorrectly, such that a low fluorescing tag is identified as being both UV2 and Starfire positive. Another example of a double call is when two tightly associated tags are identified as one by an 'Outline' macro due to insufficient tightness of the Radius Ratio setting. Additional IF/AND and COUNT functions have been used to flag up such Double and No Calls.

An alternative flowchart could examine the Fluors 1 and 4 serially, such that the final 'No' decisions from pages 2 and 4 will go on to interrogate the Starfire Red values for the relevant size tag as set forth in FIG. 6. This system can also result in a tag remaining unidentified if its size and/or fluorescence does not fall into the defined ranges. There will not be double calls with this flowchart, but this is at the risk of mis-identifying low intensity tags or doublets as described above.

Example 7

ES Cell Differentiation using Combinatorial Cell Culture and Deconvolution of Results Using Labeling Methods In Combinatorial Cell Culture, ES cell colonies grown on microscopic beads are shuffled through multiple combinations of growth conditions using random split-pool methodology accompanied by concomitant labeling. At the end of the process, any beads bearing differentiated progeny are identified and isolated; and the associated tags are analysed to deduce the cell culture history.

An example of this process is described using haematopoietic differentiation of mouse ES cells as a model system. The developmental roadmap to haematopoiesis is relatively well charted, and many of the recombinant growth factors that influence cell fate are known and readily available, nevertheless directed differentiation reported in the literature has used materials and methods (embryoid bodies; semisolid culture media; supplementation with animal serum) which are cumbersome and undefined, and which we have sought to eliminate using the experimental power of the new technique.

In particular we set out to differentiate mouse ES cells to the monocyte-macrophage (mononuclear phagocyte) lineage (Gordon S. & Taylor P. R., Nature Rev. Immunol. 2005 5: 953-964), because this has been reported to occur in vitro and because it is possible to carry out a simple functional screen for these cells based on phagocytosis of fluorescent antigens.

Materials and Methods

Reagents murine stem cell factor (SCF) (R&D Systems, 455-MC)
murine thrombopoietin (TPO) (R&D Systems, 488-TO)
human erythropoietin (EPO) (R&D Systems, 287-TC)
human interleukin 6 (IL-6) (R&D Systems, 206-IL)
human transforming growth factor □1 (TGF□1) (R&D Systems, 240-B)
murine macrophage colony stimulating factor (M-CSF) (R&D Systems, 416-ML)
murine interleukin 3 (IL-3) (R&D Systems, 403-ML)
human bone morphogenetic protein 2 (BMP2) (R&D Systems, 355-BM)
human fibroblast growth factor (bFGF) (R&D Systems, 233-FB)
retinoic acid (Sigma, R2625)
bovine insulin (Ins) (Sigma, 10516)
insulin/transferrin/selenium supplement (ITS) (Sigma, 13146)

Microculture

CULTISPHER-G microcarriers (Percell Biolytica AB) were hydrated and sterilized according to manufacturer's recommendations. Biotinylation was performed by addition of 10 mg Biotinamidohexanoyl-6-amino-hexanoic acid N-hydroxysuccinimide ester (Sigma), dissolved in 0.4 ml N,N-dimethylformamide (Sigma), to 5 ml of $Ca^{2+}/Mg^{2+}$-free PBS (CMF-PBS) containing $3\times10^5$ microcarriers and incubation overnight at room temperature, followed by 5 washes using an excess of PBS. The biotinylated microcarriers were stored in CMF-PBS.

D3 ES cells (ATTC no. CRL-1934) were grown on gelatine-coated plastic in KO-DMEM containing 15% knock-out serum replacement (KOSR), 1% non-essential amino acids (NEAA), 1% GLUTAMAX, 0.5% penicillin/streptomycin, 0.1 mM β-mercaptoethanol (β-ME; Sigma) and 1000 U/ml Leukemia Inhibitory Factor (LIF; Chemicon); all from Invitrogen unless indicated otherwise.

On the day preceding day 1 of the experiment, approximately $1.4\times10^5$ biotinylated microcarriers equilibrated in medium A (IMDM (Gibco), 15% KOSR, 1% NEAA, 0.5% pen/strep, 0.1 mM □-ME, 1000 U/ml LIF and $1.5\times10^4$ M1-thioglycerol (MTG; Sigma)) were added to 100 ml of medium A containing $3\times10^7$ ES cells, aliquoted equally into wells of a 100 mm square petri dish (25 wells; Bibby Sterilin) and incubated overnight.

An aliquot of seeded microcarriers (~100 beads) were fixed in 4% paraformaldehyde (Sigma) for 10 min at RT, washed and re-suspended in PBS, and stained with Vector Blue Alkaline Phosphatase Substrate Kit III (Vector Laboratories) according to the manufacturer's instructions.

Combinatorial Cell Culture

Seeded microcarriers were transferred into a 70 μm nylon cell strainer (Falcon) and washed with 15 ml PBS, then transferred into an excess of medium B (Stemline™ Haematopoietic Expansion Medium (Sigma) containing $1.5\times10^{-4}$ M MTG). On days 1, 4, 6, 8 and 10 microcarriers were split equally as required by the experimental plan and each sample incubated in wells of a 100 mm, 25 well, square petri dish such that each well was loaded with approx. 5000 beads in 4 ml medium B containing the relevant chemicals and/or growth factors, and $1\times10^6$ streptavidin-coated microsphere tags. This procedure was followed for each split-pool cycle except following the split on D10, when microcarriers were not tagged. Following D10, the microcarriers were processed separately (i.e. not pooled) so tagging was not required.

On day 13 of the experiment, 1 mg of the macrophage assay reagent DQ-ovalbumin (Molecular Probes) was made up in 0.4 ml PBS and added to each sample at a dilution of 1:100. Following incubation for at least 4 h, the medium was aspirated and replaced with PBS. The samples were examined on a Nikon TE2000-S inverted epifluorescent microscope using a FITC filter set to identify microcarriers bearing large, round cells internally labelled with green fluorescence.

Positive microcarriers were transferred by pipette into the well of a 384 well glass-bottom assay plate (Bibby Sterilin) containing a solution of proteinase K (2 U/ml; Sigma) in PBS and incubated at 37° C. for 30 min, following which time fluorescent tags could be seen arrayed on the glass surface.

Tags

A set of 50 tags (FIG. 13), each set comprising a population of fluorescent, streptavidin-coated polystyrene microspheres, was commissioned from Bangs Laboratories (Fishers, Ind.). The difference between the 50 sets was a function of the microsphere diameter (sized at 1.87 µm, 4.41 µm, 5.78 µm, 7.37 µm or 9.77 µm) and fluorescence emission/brightness (dyed with five intensities of either Starfire Red or UV2). Aliquots of these 50 sets were further conjugated with tetramethylrhodamine-5-(and-6)-isothiocyanate (TRITC; Invitrogen) according to the manufacturer's instructions, to produce a maximum of 100 discrete tags. From these, a set of 28 highly distinctive tags were used in the experiment (Table 1).

Tag Analysis

Tags were analysed by microscopy using a Nikon TE2000-S inverted epifluorescent microscope equipped with filter sets for visualization of the fluorophores TRITC, DAPI (UV2), GFP-B (all from Nikon) and Cy5 (Chroma Technology). Images were captured using an Evolution VF cooled monochrome camera and image analysis was using Image Pro Plus (both from Media Cybernetics). The outlines of single microspheres were captured using bright field illumination and the areas within these calculated to size the tags. The areas' fluorescence intensities in the UV2, Cy5 and TRITC channels were used to further specify the identity of each tag by comparison to reference samples containing known tags (e.g. FIG. 14).

Results

An experimental matrix of cell culture conditions is devised which we hypothesised contained one or more pathways capable of directing ES cell differentiation to macrophage (Table 1). The matrix was comprised of six alternative culture conditions on the first day (D1) of the experiment, followed by six alternative conditions on D4, a further eight on D6, eight more on D8 and finally six alternatives on D10. The total number of possible pathways through this matrix, i.e. the number of different combinations of cell culture conditions tested, was 13,824 (=6×6×8×8×6=the 'experimental complexity'). All conditions were based on a commercially available medium which permits growth of human haematopoietic progenitors, but varied in supplementation with different growth factors and morphogens known to influence mesoderm formation, haematopoietic development and commitment to the macrophage lineage (Kaushansky K., N. Engl. J. Med. 2006 354: 2034-2045; Godin I. & Cumano A. 2002 2: 593-603).

Pluripotent mouse ES cells were seeded on biotinylated macroporous gelatine microcarrier beads in the presence of LIF, where they formed cell colonies that stained positive for alkaline phosphatase activity (FIG. 8). Following LIF withdrawal, the beads were systematically passaged through all possible combinations of conditions specified in the experimental matrix using an iterative split-pool methodology as described in WO 04013969.

At the beginning of the experiment approximately $1.4\times10^5$ seeded microcarrier beads were split randomly into six sets, each of which was cultured separately in one of the six different media specified for D1 in the matrix. Four days later the beads were washed, pooled, and randomly split again into six sets each of which was cultured in one of the media specified on D4; and this split-pool procedure repeated on D6, D8 and D10. Each time an aliquot of beads was cultured in a different medium, those beads were labelled with a unique tag; except on D10, following which the split aliquots were handled separately and therefore did not require labelling. Thus, the movement of any given bead through the various culture media could be inferred by analysing the collection of tags associated with it. The labelling strategy we employed involved an array of uniquely distinctive, streptavidin-coated fluorescent microsphere tags which bound to the biotinylated microcarrier substrate.

At the end of the experiment, D13, the microcarriers were exposed to a hyper-fluoresceinated (self-quenched) ovalbumin antigen. This reagent is known to be specifically internalised and digested by phagocytic macrophages, thus dispersing the fluorophore and giving rise to a bright, intracellular signal (FIGS. 9 & 10). On screening the beads we found that approximately 100 (i.e. 0.07% of the $1.4\times10^5$ input beads) bore large, round, internally fluorescent cells. It was assumed that these beads had been passaged through conditions that were either permissive or instructive for ES cell differentiation to macrophage. Beads carrying large numbers of macrophages were analysed to deconvolute their cell culture history: these beads were isolated and the gelatine substrate proteolysed to release bound tags, which were categorised using fluorescence microscopy followed by image analysis.

Some microcarriers were labelled with large numbers of tags, all of which could be unambiguously categorised into four different species, revealing the pathway of these beads through the experimental matrix. For instance, bead C5 was found to have tags corresponding to the pathway 1.2→4.2→6.1→8.2 and was isolated from the group of beads finally partitioned into condition 10.5 (FIG. 11a).

Some other microcarriers (e.g. bead A22) were labelled with large numbers of tags, of which the majority fell into the four different species acquired through labelling, and a small minority appeared to be acquired through adventitious transfer between different microcarriers (FIG. 11b). In most of these latter cases, there was a large excess of one class of tag, which allowed a measure of confidence in deconvoluting the cell culture history. In a few cases (normally where overall labelling was inefficient, e.g. bead E6) there were equal numbers of tags from two different species added on the same day, giving rise to an ambiguity (FIG. 11c). Both these types of ambiguities were easily resolved on further experimentation to validate the results, as described below.

A batch of pluripotent mES cells seeded on microcarriers was divided into a series of aliquots, each of which was used to test one putative differentiation pathway as defined by Combinatorial Cell Culture. Ambiguous pathways (e.g. A22 and E6) were tested by assaying each alternative in parallel. Using this method, bead A22 was determined to have passed through conditions 1.2→4.2→6.4→8.2→10.3. Similarly, the route of bead E6 through the matrix was 1.2→4.2→6.3→8.4→10.5.

It is interesting that these pathways which produced macrophage had certain conditions in common. In particular, treatments on D1 and D4 were consistent in all three, possibly revealing a requirement for those conditions in the generation of haematopoietic progenitors using this system. When reproduced, these pathways consistently resulted in 10-25% of all microcarriers being decorated with substantial numbers of macrophages (FIG. 12). Deviations from the optimal pathways were found to be generally detrimental to macrophage differentiation. Similarly, when random pathways through the matrix were tested for the ability to produce macrophage, no effective protocols were found suggesting that these are relatively rare.

Conclusions

An example of mES cell differentiation is described using Combinatorial Cell Culture featuring the use of labels or tags. The process was used to screen an experimental matrix comprising almost 14,000 different cell culture protocols for conditions leading to differentiation to the monocyte-macrophage lineage. By screening such a large number of potential pathways and using a suitable labeling strategy it was possible to identify multiple differentiation protocols, and to overcome the use of embryoid bodies and animal serum, one or both of which are normally required for monocyte-macrophage development in vitro.

Example 8

Digestion of Cultispher-G Microcarriers on Glass Slides for Tag Deconvolution

Reagents and Equipment
  Proteinase K (Sigma P4850 1 ml)
  Sigmacote (Sigma SL-2)
  Glass microscope slides
  68° C. oven
  Home-made humidified box
  Glycerol (or Citifluor)
  Forceps
  13 mm-diameter glass coverslips
Methods
  Microcarriers are digested individually to reveal the complement of tags that are attached. Digestion is carried out on a glass microscope slide (can digest up to 6 microcarriers on one slide)
    Coat glass microscope slides with Sigmacote in fume hood: holding slide horizontally, carefully pipette 1 ml of Sigmacote onto the top of the slide, ensuring that it covers the entire glass surface. Leave in place for approx 30 s and then carefully tip the slide and remove the Sigmacote from the edge with a pipette. The sigmacote may be re-used so return to the bottle. Most of the Sigmacote is removed in this way but do allow any remaining Sigmacote to evaporate completely. If there are any traces of Sigmacote left on the slide or if there are any smears, wipe the surfaces of the slide with gloved fingers to produce clean surfaces on the slide
    Ensure that microcarriers to be digested have been carefully washed in $dH_2O$ to remove any traces of medium and/or salts. Using a 20 µl pipette tip, carefully remove individual microcarriers from the $dH_2O$ in a minimal volume (1-2 µl max) and deposit on the glass slide. It is not always necessary to pipette the whole 1-2 µl volume onto the slide; just pipette enough to deposit the microcarrier on the slide (ensure the microcarriers are sufficiently spaced to allow later addition of a coverslip without overlap—5-6 microcarriers per slide is achievable with care)
    Carefully place the slides in a 68° C. oven to achieve complete dehydration of the microcarriers and sticking to the slide (10 mins should suffice).
    Make a fresh 5 U/ml solution of proteinase k in $dH_2O$ (note that the concentration of proteinase k stock varies between batches so the dilution should be calculated with each new batch (e.g. Stock solution 1230 U/ml to 5 U/ml=5/1230=1/246. i.e. 1 in 246 dilution of stock solution in $dH_2O$)
    Prepare a humidified box in which the digestion reaction will be performed (a 10 cm×10 cm cell culture Petri works well with disposable plastic pipettes cut to size to fit along 2 sides. Place water-wetted tissue inbetween the pipettes)
    Carefully but quickly pipette 0.5 µl of 5 U/ml proteinase k solution directly onto the dried microcarriers (this can be quite fiddly as 0.5 µl is a very small volume and will evaporate quickly outside the humidified box). Once all the microcarriers have had proteinase k added to them, place the slide in the humidified box and cover with a lid. Leave at room temperature, protected from light as much as possible, until the microcarriers have dissolved (typically 30-60 mins). It is necessary to remove the slides from the humidified box to check for complete digestion and this needs to be performed as quickly as possible before immediate return of the slides to the box to avoid evaporation of proteinase k soln)
    Once satisfied that the microcarriers have completely dissolved, remove the slides from the box and allow to sit at room temp to allow evaporation of the proteinase k soln (this will proceed quite quickly). Place the slides in a 68° C. oven for approx 10 mins to ensure complete drying of the released tags onto the slide).
    Carefully add a 6 µl drop of glycerol directly to the dried tags, taking care to avoid air bubbles (if air bubbles are present in the drop it is often easy to remove them by pricking with a small needle). Using forceps, carefully lower a dust-free, 13 mm-diameter coverslip onto the glycerol droplet, taking extreme care to avoid air bubbles (it is almost impossible to remove air bubbles from under the coverslip once in place). Allow the coverslip to settle (the glycerol will spread throughout the entire coverslip. Protect slides from light as much as possible but be careful not to disturb the coverslips too much and spread glycerol over the surface.
  Analyse tags using a microscope.

Example 9

Digestion of CYTOPORE 2 Microcarriers

Reagents and Equipment
  Lab coat, safety glasses, gloves
  *Hydrochloric acid, 37%
  Petri dish
  Thin-walled PCR tubes
  Sigmacote (Sigma cat #SL-2)
  Citifluor mounting medium (Agar scientific)
Method
  Following a split-pool experiment, microcarriers are digested individually to reveal the complement of tags that are attached. Digestion of individual microcarriers is carried out in a thin-walled PCR tube in a thermal cycler or heater block at 65° C.

1. Draw individual CYTOPORE-2 microcarrier+tags (+cells) into pipette tip in smallest volume possible, typically <2 µl (20 µl pipette and tip work well) and deposit into 5 µl drop of 37% HCl in petri dish. Move quickly to next step . . . .
2. Quickly draw up the microcarrier into a pipette tip set to 1 µl and deposit into the very bottom of a thin-walled PCR tube and close the lid.
3. Place the tube in a thermal cycler or heater block set at 65° C. for 7 mins (check that the carrier has dissolved by inspection through the tube wall using a microscope and increase time by another 2 mins if necessary. Carrier should have dissolved after 7-9 mins).
4. Treat glass microscope slide with Sigmacote.
5. Treat 2 µl pipette tip with sigmacote, ensuring that it dries completely, before carefully removing the HCL in the PCR tube containing the tags.
6. Deposit 1 µl droplet onto microscope slide. Invert so drop is hanging drop and incubate in 68° C. dry over until completely dry (15-30 mins). Add drop of Citifluor and coverslip. Analyse tags using a microscope.

Example 10

Labelling Cell Units with Rod-Shaped Tags

3500 CULTISPHER G microcarriers were seeded with D3 mouse ES cells in a single cell suspension at a density of 50 cells per carrier in 2 ml growth medium comprising KO-DMEM+15% KO-SR, 100 U/ml penicillin, 50 µg/ml streptomycin, 2 mM GLUTAMAX, 1×NEAA, 1000 U/ml LIF, 100 µM βME, and the cell units cultured overnight at 37° C.

Neutral red vital staining was performed on the cell units prior to addition of nanobarcode particles to confirm viability of cells before particle addition.

Suspensions of rod-shaped particles comprising 6 micron-long Ag/Au coated aluminium nanowires (Nicewarner-Pena, S. R. et al., Science 294: 137-141, 2001) were obtained from Oxonica Healthcare (Kidlington, UK) at a concentration of $1 \times 10^9$ particles per ml. Two barcodes designated 101010 and 100001 (where 1=Ag and 0=Au) were used to label the cell units.

A sample of the rod-shaped particles was removed from the stock and sterilised in 95% ethanol for 1 hr before washing and resuspension in sterile PBS. A mixture of the two nanobarcode particles was added to ~875 cell units in 2 ml medium in a well of a 25-well cell culture dish at a ratio of 1000 particles per cell unit. The cell culture dish was incubated at 37° C. overnight on an orbital shaker.

After 24 hours in culture the labelled cell units were placed on a 70 cm filter to remove unbound rod-shaped particles and washed 5 times with 5 ml PBS. Individual cell units were removed and the continued viability of the D3 cells in the presence of the rod-shaped particles assessed by neutral red vital stain.

Individual cell units were deposited on Sigmacote-treated glass microscope slides and placed at 68° C. for 10-15 mins to ensure complete dehydration. Fresh 5 U/ml proteinase k in $H_2O$ was prepared and 0.5 µl deposited directly on the dehydrated material. Slides were immediately placed in a humidified chamber until the gelatine material had digested (typically 30-60 mins) and then removed to a 68° C. incubator to allow complete evaporation of the proteinase k solution (typically 10 mins).

A 5 µl drop of glycerol was applied directly to the dried spot and a 13 mm round coverslip applied. Microscopic images of the released rod-shaped particles were captured using brightfield illumination with a Nikon TE2000S inverted epifluorescent microscope.

Discrimination of the rod-shaped particles in the sample was achieved using a Deltavision RT microscope equipped with a Hg lamp and a Chroma CFP filter set (Ex. 436/10; Em. 465/30) with a 100× oil immersion objective.

Further Aspects

Further aspects and embodiments are presented in the following numbered paragraphs.

1. A complex comprising a microcarrier and a microsphere or microbead.
2. The complex according to paragraph 1, wherein the microcarrier is a CULTISPHER-G microcarrier or a CYTOPORE 2 microcarrier.
3. The complex according to paragraph 1 or paragraph 2, wherein the microsphere or microbead is a fluorescent and/or coloured microsphere or microbead.
4. The complex according to any of the preceding paragraphs, wherein the microcarrier is biotinylated.
5. The complex according to paragraph 4, wherein the fluorescent microsphere is a hydrophilic microsphere.
6. The complex according to paragraph 5, wherein the hydrophilic microsphere is a carboxylate modified (CML) microsphere.
7. The complex according to paragraph 6, wherein the complex comprises a CYTOPORE 2 microcarrier and a CML microsphere.
8. The complex according to paragraph 7, wherein the ratio of CML microsphere: a CYTOPORE 2 microcarrier is about 1:1.
9. The complex according to any of paragraphs 1-4, wherein the microbead is a polystyrene microbead.
10. The complex according to any of paragraphs 1-4 and 9, wherein the microbead is streptavidin-coated.
11. The complex according to paragraph 10, wherein the complex comprises a CULTISPHER-G microcarrier and a polystyrene microbead.
12. The complex according to any of paragraphs 3-11, wherein the fluorophore is TRITC.
13. A method for separating a complex comprising a CULTISPHER-G microcarrier and a microsphere, comprising the step of contacting said complex with proteinase K.
14. The method according to paragraph 13, wherein the proteinase K is used in an amount of 2 U/ml.
15. The method according to paragraph 13 or paragraph 14, wherein the complex is contacted with proteinase K for about 20 minutes.
16. A method for separating a complex comprising a CYTOPORE 2 and a microbead, comprising the step of contacting said complex with HCl.
17. The method according to paragraph 16, wherein 37% HCl (~12M) is used.
18. The method according to paragraph 16 or paragraph 17, wherein the complex is contacted with HCl for about 90 minutes
19. A method for determining the effect of a plurality of culture conditions on a cell comprising the use of a complex according to any of paragraphs 1-12.
20. A method for determining the effect of a plurality of culture conditions on a cell, comprising the steps of:
(a) providing a first set of groups of cell units each comprising one or more cells, and exposing said groups to desired culture conditions;

(b) subdividing one or more of said groups to create a further set of groups of cell units;
(c) exposing said further groups to further desired culture conditions;
(d) optionally, repeating steps (b)-(c) iteratively as required; and
(e) assessing the effect on a given cell unit of the culture conditions to which it has been exposed,
wherein each cell unit comprises one or more cells adherent to or bounded by a complex according to any of paragraphs 1-12.

21. A method for determining the effect of a plurality of culture conditions on a cell, comprising the steps of:
a) providing a first set of groups of cell units each comprising one or more cells, and exposing said groups to desired culture conditions;
(b) pooling two or more of said groups to form at least one second pool;
(c) subdividing the second pool to create a further set of groups of cell units;
(d) exposing said further groups to desired culture conditions;
(e) optionally, repeating steps (b)-(d) iteratively as required; and
(f) assessing the effect on a given cell unit of the culture conditions to which it has been exposed,
wherein each cell unit comprises one or more cells adherent to or bounded by a complex according to any of paragraphs 1-12.

22. A method for exposing a cell to a variety of cell culture conditions, comprising the steps of:
a) providing a first set of groups of cell units each comprising one or more cells, and exposing said groups to desired culture conditions;
(b) pooling two or more of said groups to form at least one second pool;
(c) subdividing the second pool to create a further set of groups of cell units;
(d) exposing said further groups to desired culture conditions; and
(e) optionally, repeating steps (b)-(d) iteratively as required, wherein each cell unit comprises one or more cells adherent to or bounded by a complex according to any of paragraphs 1-12.

23. A method for determining the effect of a plurality of culture conditions on a cell, comprising the steps of:
(a) providing a first set of groups of cell units each comprising one or more cells, and exposing said groups to desired culture conditions;
(b) pooling two or more of said groups to form at least one second pool;
(c) subdividing the second pool to create a further set of groups of cell units;
(d) exposing said further groups to desired culture conditions;
(e) optionally, repeating steps (b)-(d) iteratively as required; and
(f) assessing the effect on a given cell unit of the culture conditions to which it has been exposed,
wherein each cell unit comprises one or more cells adherent to or bounded by a complex according to any of paragraphs 1-12.

24. A method according to any of paragraphs 20-23, wherein the cells are cultured in cell units, each cell unit comprising one or more cells.

25. A method according to paragraph 24, wherein the cell units are single cells.

26. A method according to any of paragraphs 20-25, wherein the culture conditions are media to which the cell is exposed.

27. A method according to paragraph 26, wherein the media contain one or more specific agents which influence a cellular process.

28. A method according to any of paragraphs 20-27, wherein the cell culture conditions comprise culturing at one or more specific temperatures.

29. A method according to any of paragraphs 20-28, wherein the cell culture conditions comprise culturing on one or more specific substrates.

30. A method for identifying a gene which influences a cellular process, comprising the steps of:
a) determining the effect of one or more culture conditions on a cell unit, in accordance with any one of paragraphs 20-29;
b) analysing gene expression in said cell units when exposed to said culture conditions; and
c) identifying genes which are differentially expressed under desired culture conditions.

31. A method according to paragraph 30, wherein the desired culture conditions influence a cellular process.

32. A method for producing a nucleic acid which encodes a gene product which influences a cellular process, comprising identifying a gene in accordance with paragraph 30 or paragraph 31, and producing at least the coding region of said gene by nucleic acid synthesis or biological replication.

33. A method for inducing a cellular process, comprising the steps of:
(a) identifying one or more genes which are differentially expressed in association with the cellular process in accordance with paragraph 30 or paragraph 31; and
(b) modulating the expression of said one or more genes in the cell.

34. A method according to paragraph 33, wherein modulation of gene expression in the cell comprises transfection of said one or more genes into the cell.

35. A method according to paragraph 33, wherein modulation of gene expression comprises the exogenous administration of a gene product.

36. A method for identifying the state of a cellular process of a cell, comprising the steps of:
(a) identifying one or more genes which are differentially expressed in association with the cellular process in accordance with paragraph 30 or paragraph 31; and
(b) detecting the modulation of expression of said one or more genes in a cell, thereby determining the state of the cellular process of said cell.

37. A method according to paragraph 36, wherein said one or more genes encode a marker.

38. A method according to paragraph 37, wherein said marker may be detected by an immunoassay.

39. A method for inducing a cellular process, comprising the steps of:
(a) determining the effect of one or more culture conditions on a cell unit, in accordance with any one of paragraphs 20 to 29;
(b) exposing a cell to culture conditions which induce the cellular process; and
(c) isolating the desired cell.

40. A method for identifying an agent which is capable of inducing a cellular process, comprising the steps of:
(a) determining the effect of one or more agents on a cell unit, in accordance with any one of paragraphs 20 to 29; and
(b) identifying those agent(s) which induce the cellular process in the cell units.

41. A method for preparing an agent which is capable of inducing a cellular process, comprising the steps of:
(a) determining the effect of one or more agents on a cell unit, in accordance with any one of paragraphs 20 to 29;
(b) identifying those agent(s) which induce the desired cellular process in the cell units; and
c) synthesising or isolating the agent(s).

42. A method according to any of the preceding claims, wherein the cellular process is cell proliferation or differentiation.

43. A method for culturing stem cells or cells that have been derived from stem cells in vitro comprising the steps of:
a) incubating a stem cell culture; and
b) splitting said culture into two or more groups of stem cells, and culturing said group of stem cells under two or more different sets of culture conditions
wherein each cell unit comprises one or more cells adherent to or bounded by a complex according to any of paragraphs 1-12.

43. A method according to paragraph 43, wherein the cells are cultured in cell units, each cell unit comprising one or more cells.

44. A method according to paragraph 42 or paragraph 43, wherein the cell units are single cells.

45. A method for culturing stem cells, comprising growing said stem cells adhered to a complex according to any of paragraphs 1-12.

46. A method according to paragraph 45, wherein said stem cells are subjected to at least one change of culture conditions.

47. A method according to paragraph 46, wherein said change of culture conditions comprises a change of medium.

48. A method for obtaining differentiated cells from stem cells in vitro, comprising the steps of:
(a) growing stem cells adherent to the complex according to any of paragraphs 1-12 in a culture medium;
(b) transferring the complex from one culture medium to another;
(c) optionally repeating step (b) as required; and
(d) obtaining the differentiated cells attached to the complex.

49. A method according to paragraph 48, wherein the differentiated cells are isolated by enzymatic or chemical detachment from the complex.

50. A method according to paragraph 49, wherein the enzyme is proteinase K.

51. A method according to paragraph 49, wherein the chemical is HCl.

52. A method according to any of paragraphs 48 to 51, wherein the differentiated cells are isolated by digestion of the complex according to any of paragraphs 1-12.

53. A method of growing pluripotent stem cells in vitro comprising the steps of:
(a) seeding said cells on the complex according to any of paragraphs 1-12; and
(b) propagating the cells while attached to the complex.

54. A method for identifying one or more area and/or density values for a tag obtained from a cell unit comprising the steps of:
(a) obtaining one or more images of the tag;
(b) drawing outlines for the one or more images;
(c) loading the outlines for the one or more images; and
(d) reading the area and/or brightness within the one or more outlines.

55. A method for identifying one or more area and/or density values for a tag obtained from a cell unit comprising the steps of:
(a) separating the cell unit and the tag;
(b) obtaining one or more images of the tag using a microscopic technique;
(c) drawing outlines for the one or more images;
(d) loading the outlines for the one or more images onto further corresponding images obtained using a different microscopic technique; and
(e) reading the area and/or brightness within the one or more outlines.

56. A method according to paragraph 55, wherein step (e) comprises counting and/or classifying one or more different tags in one or more cell units.

57. A method according to paragraph 54 or 55, wherein the method comprises counting and/or classifying at least different types of tags in one or more cell units.

58. A method according to paragraph 54 or 55, wherein the method comprises counting and/or classifying up to about 10 or up to about 50 different types of tags in one or more cell units.

59. A method according to any of paragraphs 54-58, wherein the area and/or density values are inputted into a spreadsheet.

60. A method according to any of paragraphs 54-59, wherein the image is selected from the group consisting of a phase image, a blue image, a green image, a near red image and a far red image.

61. A computer program product including a computer program for controlling a computer to perform a method as claimed in any one of paragraphs 54-60.

62. An apparatus for identifying one or more area and/or density values for a tag, said apparatus comprising data processing logic operable to perform data processing operations in accordance with a method as claimed in any one of paragraphs 54-60.

63. A method for determining the chronology and identity of the cell culture conditions to which a cell unit has been exposed comprising the steps of:
(a) comparing the upper and lower limits of at least one parameter of a tag with the mean measurement of the at least one parameter of the tag;
(b) comparing the mean measurement for the at least one parameter of the tag with the lowest limit for the at least one parameter of the tag; and
(c) correlating the measurement of the at least one parameter of the tag with the identity of the tag associated with the cell unit.

64. A method according to paragraph 63, wherein if the lower limit is less than the mean measurement and the mean measurement is less then than the upper limit then the upper and lower limits of a further parameter of the tag are compared with the mean measurement for at least one further parameter of the tag.

65. A method according to paragraph 63, wherein if the lower limit is not less than the mean measurement and the mean measurement is not less then than the upper limit then the upper and lower limits of at least one further integer of the same parameter of the tag is measured.

66. A method according to paragraph 65, wherein if the lower limit is less than the mean measurement and the mean measurement is less then than the upper limit then the at least one further parameter for the tag is measured.

67. A method according to any of paragraphs 63-66, wherein if the mean measurement for the at least one parameter of the tag is greater than the lowest limit for at least one parameter of the tag, then the result is correlated with one or more tags that possess the one or more parameters.

68. A method according to any of paragraphs 63-66, wherein if the mean measurement for the at least one parameter of the tag is not greater than the lowest limit for the one or more parameters of the tag, then the result is correlated with a tag that possess the parameter.

69. A method according to paragraph 63, wherein if the lower limit is not less than the mean measurement and the mean measurement is not less then than the upper limit for the at least one further parameter then the upper and lower limits of at least one further integer of the same parameter of the tag is measured.

70. A method according to paragraph 68, wherein the method is repeated for one or more further integers of the same parameter of the tag.

71. A method according to paragraph 69, wherein the method is repeated for all integers of the same parameter of the tag.

72. A method according to paragraph 68, wherein if the lower limit is less than the mean measurement and the mean measurement is less then than the upper limit for the at least one further parameter and the mean measurement for the at least one parameter of the tag is greater than the lowest limit for at least one parameter of the tag, then the result is correlated with one or more tags that possess the one or more parameters.

73. A method according to paragraph 71, wherein if the lower limit is less than the mean measurement and the mean measurement is less then than the upper limit for the at least one further parameter and the mean measurement for the at least one parameter of the tag is not greater than the lowest limit for the one or more parameters of the tag, then the result is correlated with a tag that possess the parameter.

74. A method according to any of paragraphs 62-72, wherein the parameter(s) of the tag are selected from the group consisting of size of the tags, the type of fluorophore that they carry; and the quantity of fluorophore that they carry.

75. A method according to paragraph 73, wherein the sizes are selected from 5 different sizes.

76. A method according to paragraph 73 or paragraph 74, wherein the sizes are selected from the group consisting of about 1.87 µm, about 4.41 µm, about 5.37 µm, about 5.78 µm and about 9.66 µm.

77. A method according to any of paragraphs 73-75, wherein the fluorophore is either UV2 or Starfire Red.

78. A method according to any of claims 73-75, wherein the quantity of fluorophore is selected from 5 different quantities.

79. A method according to paragraph 77, wherein each different quantity gives a 5 to 10-fold difference in brightness.

80. A method according to any of paragraphs 62-79, wherein there are up to 3 different parameters and 50 different integers or populations.

81. A method complex according to any of paragraphs 62-79, wherein each cell unit comprises one or more cells adherent to or bounded by a complex comprising a microcarrier and a polystyrene microbead.

82. A method according to paragraph 80, wherein the microbead is streptavidin-coated.

83. A method according to paragraph 80 or paragraph 81, wherein the complex comprises a CULTISPHER-G microcarrier and a polystyrene microbead.

84. A computer program product including a computer program for controlling a computer to perform a method as claimed in any one of paragraphs 62-82.

85. An apparatus for determining the chronology and identity of the cell culture conditions to which a cell unit has been exposed, said apparatus comprising data processing logic operable to perform data processing operations in accordance with a method as claimed in any one of paragraphs 62-82.

TABLE 1

| Tag | Ø | Fluor | [Fluor] | ±TRITC | Additions to Basal Medium |
|---|---|---|---|---|---|
| 1.1 | 4.4 | UV | 4 | − | 10 nM RA |
| 1.2 | 4.4 | SR | 2 | − | 0.1% (v/v) DMSO |
| 1.3 | 4.4 | UV | 2 | − | 1000 U/ml LIF + TGFβ1 + 5 ng/ml BMP2 |
| 1.4 | 7.4 | SR | 5 | + | 1000 U/ml LIF + 10 ng/ml bFGF |
| 1.5 | 7.4 | UV | 4 | + | 1000 U/ml LIF + 20 ng/ml TPO |
| 1.6 | 7.4 | UV | 2 | + | 1000 U/ml LIF |
| 4.1 | 4.4 | SR | 2 | + | 2.5 ng/ml TGFβ1 |
| 4.2 | 9.8 | UV | 2 | − | 10 µg/ml Ins |
| 4.3 | 9.8 | UV | 2 | + | 2.5 ng/ml TGFβ1 + 5 ng/ml BMP2 |
| 4.4 | 4.4 | SR | 4 | − | 40 ng/ml SCF |
| 4.5 | 7.4 | SR | 4 | + | 20 ng/ml TPO |
| 4.6 | 9.8 | UV | 1 | + | 10 µg/ml ITS |
| 6.1 | 4.4 | SR | 1 | − | 30 ng/ml IL3 + 20 ng/ml IL6 |
| 6.2 | 7.4 | UV | 4 | − | 30 ng/ml IL3 + 20 ng/ml IL6 + 3 U/ml EPO + 10 ng/ml M-CSF |
| 6.3 | 9.8 | UV | 3 | + | 10 µg/ml ITS + 3 U/ml EPO |
| 6.4 | 7.4 | UV | 1 | + | 10 µg/ml ITS + 10 ng/ml M-CSF |
| 6.5 | 4.4 | UV | 5 | − | 20 ng/ml TPO + 3 U/ml EPO |
| 6.6 | 7.4 | SR | 3 | + | 20 ng/ml TPO + 10 ng/ml M-CSF |
| 6.7 | 4.4 | UV | 3 | − | 30 ng/ml IL3 + 20 ng/ml IL6 + 3 U/ml EPO |
| 6.8 | 9.8 | UV | 5 | − | 30 ng/ml IL3 + 20 ng/ml IL6 + 10 ng/ml M-CSF |
| 8.1 | 4.4 | SR | 3 | − | 30 ng/ml IL3 + 20 ng/ml IL6 |
| 8.2 | 7.4 | SR | 5 | − | 30 ng/ml IL3 + 20 ng/ml IL6 + 3 U/ml EPO + 10 ng/ml M-CSF |
| 8.3 | 9.8 | UV | 1 | − | 10 µg/ml ITS + 3 U/ml EPO |
| 8.4 | 7.4 | UV | 2 | − | 10 µg/ml ITS + 10 ng/ml M-CSF |
| 8.5 | 7.4 | SR | 3 | − | 20 ng/ml TPO + 3 U/ml EPO |
| 8.6 | 4.4 | SR | 5 | − | 20 ng/ml TPO + 10 ng/ml M-CSF |
| 8.7 | 9.8 | UV | 3 | − | 30 ng/ml IL3 + 20 ng/ml IL6 + 3 U/ml EPO |
| 8.8 | 4.4 | UV | 4 | + | 30 ng/ml IL3 + 20 ng/ml IL6 + 10 ng/ml M-CSF |
| 10.1 | | | | | 30 ng/ml IL3 + 20 ng/ml IL6 |
| 10.2 | | | | | 30 ng/ml IL3 + 20 ng/ml IL6 + 3 U/ml EPO + 10 ng/ml M-CSF |
| 10.3 | | | | | 20 ng/ml TPO + 3 U/ml EPO |
| 10.4 | | | | | 20 ng/ml TPO + 10 ng/ml M-CSF |

TABLE 1-continued

| Tag | Ø | Fluor | [Fluor] | ±TRITC | Additions to Basal Medium |
|---|---|---|---|---|---|
| 10.5 | | | | | 30 ng/ml IL3 + 20 ng/ml IL6 + 3 U/ml EPO |
| 10.6 | | | | | 30 ng/ml IL3 + 20 ng/ml IL6 + 10 ng/ml M-CSF |

Legend to Table 1

List of the conditions comprising the experimental matrix, and the corresponding tags used to label microcarriers exposed to those conditions. Tag nomenclature denotes the day of the experiment and the experimental condition (day.condition). Columns 2-5 list the characteristics of the corresponding tag, i.e. size (diameter); fluorophore identity (UV2 or Starfire Red); fluorophore intensity (1 lowest-5 highest) and whether the tag was TRITC modified. For each condition of the matrix, the final concentrations of the different growth factors and/or morphogens present in the basal medium are indicated in the final column.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A complex composition comprising a microcarrier having a net charge, conjugated to a charged particulate tag having optically detectable properties, wherein the microcarrier comprises a material selected from the group consisting of protein, cellulose, polyethylene, polystyrol, glass, collagen, collagen-glucose-aminoglycan and/or gelatin, and wherein the microcarrier having the charged particulate tag conjugated thereto is configured for adherence by a cell unit in a culture system.

2. The complex composition according to claim 1, wherein the microcarrier is a porous microcarrier.

3. The complex composition according to claim 1, wherein the tag is negatively charged.

4. The complex composition according to claim 1, wherein the charged tag is a sphere.

5. The complex composition according to claim 4, wherein the sphere is a microsphere.

6. The complex composition according to claim 5, wherein the microsphere is about 9 µM or less in diameter.

7. The complex composition according to claim 5, wherein the microsphere is a carboxylate modified (CML) microsphere.

8. The complex composition according to claim 1, wherein the tag comprises polystyrene and/or latex.

9. The complex according to claim 1, wherein the complex is adhered or bound to a cell unit.

10. The complex composition according to claim 9, wherein at least one antibody is bound to the cell unit.

11. A method for determining the effect of a plurality of culture conditions on a cell, comprising the steps of:
(a) providing a first set of groups of cell units each comprising one or more cells, and exposing said groups to specific predefined culture conditions;
(b) pooling two or more of said groups to form at least one second pool;
(c) subdividing the second pool to create a further set of groups of cell units;
(d) exposing said further groups in step c) to further specific predefined culture conditions;
(e) optionally, repeating steps (b)-(d) iteratively as required; and
(f) assessing the effect on a given cell unit of the different specific predefined culture conditions to which it has been exposed, wherein each cell unit comprises one or more cells adherent to or bounded by a complex composition according to claim 1.

12. The method according to claim 11, wherein the cells are cultured in cell units, each cell unit comprising one or more cells.

13. The method according to claim 12, wherein the cell units are single cells.

14. The method according to claim 11, wherein the culture conditions are media to which the cell is exposed.

15. The method according to claim 14, wherein the media contain one or more specific agents which influence a cellular process.

16. The method according to claim 11, wherein the cell culture conditions comprise culturing at one or more specific temperatures.

17. The method according to claim 11, wherein the cell culture conditions comprise culturing on one or more specific substrates.

18. The method according to claim 11, further charged particulate tags from the complex composition.

19. The method according to claim 18, wherein the tags are separated by exposing the complex composition to an acid, a protease or a cellulase.

20. The method according to claim 19, wherein the tag is subjected to image analysis.

21. A method for culturing stem cells or cells that have been derived from stem cells in vitro comprising the steps of:
a) incubating a stem cell culture; and
b) splitting said culture into two or more groups of stem cells, and culturing said two or more groups of stem cells under two or more different sets of specific predefined culture conditions;
wherein the cells are cultured in cell units, each cell unit comprising one or more cells adhered to or bounded by the complex composition according to claim 1.

22. The method according to claim 21, wherein the cell units are single cells.

23. The method according to claim 21, wherein said stem cells are subjected to at least one change of culture conditions.

24. The method according to claim 23, wherein said change of culture conditions comprises a change of medium.

25. A method for obtaining differentiated cells from stem cells in vitro, comprising the steps of:
(a) growing stem cells adherent to the complex composition according to claim 1 in a culture medium;
(b) transferring the complex composition from one culture medium to another;
(c) optionally repeating step (b) as required; and (d) obtaining the differentiated cells attached to the complex composition.

26. The method according to claim 25, wherein the differentiated cells are isolated by enzymatic or chemical detachment from the complex.

27. The method according to claim 25, wherein the differentiated cells are isolated by digestion of the complex.

* * * * *